(12) United States Patent
Kramer et al.

(10) Patent No.: US 11,891,517 B2
(45) Date of Patent: Feb. 6, 2024

(54) WAX COMPOSITIONS COMPRISING LINEAR OLEFIN DIMERS OR HYDROGENATED VARIANTS THEREOF AND METHODS FOR PRODUCTION THEREOF

(71) Applicant: ExxonMobil Chemical Patents Inc., Baytown, TX (US)

(72) Inventors: Anatoly I. Kramer, Baytown, TX (US); Alexander V. Zabula, Seabrook, TX (US); Elizabeth A. Turner, Ontario (CA); Raf de Meester, Temse (BE); Helge Jaensch, Grimbergen (BE); Jeffrey C. Bunquin, Houston, TX (US); Javier Guzman, Porter, TX (US); Emiel de Smit, Brussels (BE); John S. Coleman, Seabrook, TX (US); Madelyn Bekker, Houston, TX (US); Roxana Perez Velez, Leuven (BE)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 17/908,769

(22) PCT Filed: Mar. 2, 2021

(86) PCT No.: PCT/US2021/020527
§ 371 (c)(1),
(2) Date: Sep. 1, 2022

(87) PCT Pub. No.: WO2021/183327
PCT Pub. Date: Sep. 16, 2021

(65) Prior Publication Data
US 2023/0127018 A1    Apr. 27, 2023

Related U.S. Application Data

(60) Provisional application No. 62/987,504, filed on Mar. 10, 2020.

(30) Foreign Application Priority Data

May 7, 2020  (EP) .................................. 20173376

(51) Int. Cl.
C07C 6/04 (2006.01)
C08L 91/06 (2006.01)
C07C 7/163 (2006.01)

(52) U.S. Cl.
CPC ............... C08L 91/06 (2013.01); C07C 6/04 (2013.01); C07C 7/163 (2013.01); *C07C 2531/22* (2013.01)

(58) Field of Classification Search
CPC ............ C07C 6/04; C07C 7/163; C08L 91/06
See application file for complete search history.

(56) References Cited

U.S. PATENT DOCUMENTS

| 4,409,409 A | 10/1983 | Langer et al. | 585/255 |
| 6,613,910 B2 | 9/2003 | Grubbs et al. | 548/103 |

(Continued)

FOREIGN PATENT DOCUMENTS

| EP | 1395534 | 11/2002 | ............... C07C 6/04 |
| WO | WO2000/071554 | 11/2000 | ............... C07F 15/00 |

(Continued)

OTHER PUBLICATIONS

Dinger, M. B.; Mol, J. C. (2002) "High Turnover Nos. with Ruthenium-Based Metathesis Catalysts," *Advanced Synthesis & Catalysts*, v.344(6-7), pp. 671-677.

(Continued)

*Primary Examiner* — Sharon Pregler

(57) ABSTRACT

Wax compositions may be obtained by providing an olefinic feed comprising a first linear alpha olefin having m carbon atoms and a second linear alpha olefin having n carbon atoms, wherein m and n are independently selected integers each ranging from about 12 to about 100, and the olefinic (Continued)

feed optionally comprises one or more internal olefins and/or one or more branched olefins; contacting the olefinic feed with a metal carbene catalyst in a reactor; forming ethylene and a hydrocarbon substance comprising a linear olefin dimer comprising two carbon atoms less than a sum of m and n; removing the ethylene from the reactor while forming the linear olefin dimer; and isolating a wax composition comprising the linear olefin dimer, a hydrogenated reaction product thereof, or any combination thereof.

18 Claims, 2 Drawing Sheets

(56) References Cited

U.S. PATENT DOCUMENTS

| | | | |
|---|---|---|---|
| 6,838,489 B2 | 1/2005 | Bell et al. ............... 522/63 |
| 7,205,424 B2 | 4/2007 | Nolan ............... 556/136 |
| 7,683,180 B2 | 3/2010 | Grubbs et al. ............... 548/103 |
| 8,586,757 B2 | 11/2013 | Mauduit et al. ............... 548/103 |
| 8,846,939 B2 | 9/2014 | Grubbs et al. ............... 548/103 |
| 2009/0043140 A1* | 2/2009 | Yang ............... C10G 50/00 585/277 |
| 2010/0205851 A1 | 8/2010 | Uptain et al. ............... 44/275 |

FOREIGN PATENT DOCUMENTS

| | | | |
|---|---|---|---|
| WO | WO2003/101920 | 12/2003 | ............ C07C 6/04 |
| WO | WO2008/065187 | 6/2008 | ............ B01J 31/12 |
| WO | WO2013/079820 | 6/2013 | ............ C07C 6/04 |

OTHER PUBLICATIONS

DuToit, Jean I. et al. (2015) "Towards a Better Understanding of Alkene Metathesis: Elucidating the Properties of the Major Metal Carbene Catalyst Types," *Chem. Monthly*, v.146(7), pp. 1115-1129.
Hong, Soon H. et al. (2007) "Decomposition of Ruthenium Olefin Metathesis Catalysts," *J. Am. Chem. Soc.*, v.129(25), pp. 7961-7968.
Hoveyda, A. H. et al. (2007) "The Remarkable Metal-Catalysed Olefin Metathesis Reaction," *Nature*, v.450(7167), pp. 243-251.
Ivin, K. et al. (1998) "Some Recent Applications of Olefins Metathesis in Organic Synthesis: A. Review," *J. Mol. Catal. A: Chem.*, v.133, 16 pages.
Minenkov, Y. et al. (2013) "Complete Reaction Pathway of Ruthenium-Catalyzed Olefin Metathesis of Ethyl Vinyl Ether: Kinetics and Mechanistic Insight from DFT," *ACS Publication, Organometallics*, v.32(7), pp. 2099-2111.
Trinka, T. et al. (2001) "The Development of L2X2RuCHR Olefin Metathesis Catalysts: An Organometallic Success Story," *Acc. Chem. Res.*, v.34(1), pp. 18-29.

* cited by examiner

WAX COMPOSITIONS COMPRISING LINEAR OLEFIN DIMERS OR HYDROGENATED VARIANTS THEREOF AND METHODS FOR PRODUCTION THEREOF

CROSS REFERENCE TO RELATED APPLICATIONS

This application is a National Phase Application to PCT Application Serial No. PCT/US2021/020527 filed Mar. 2, 2021, which claims the priority benefit of U.S. Provisional Application No. 62/987,504, filed Mar. 10, 2020, and EP 20173376.3 filed May 7, 2020, wherein 62/987,504 and EP 20173376.3 are herein incorporated by reference.

FIELD

The present disclosure relates to wax compositions and methods for their production and use.

BACKGROUND

The global wax market has experienced significant growth over the past few years, and demand for different types of wax compositions across various industries has been steadily increasing. Waxes are hydrophobic organic substances that occur in petroleum or other oleaginous materials, and may be produced synthetically in a reactor or biosynthetically by plants and animals. Waxes are usually malleable solids at room temperature, which may comprise one or more higher alkanes, lipids and/or oils, or unsaturated variants thereof. Wax compositions include natural waxes, synthetic waxes and vegetable waxes. Traditional wax compositions in common use include, for example, paraffin wax (e.g., slack wax), beeswax, and hydrogenated vegetable oils (e.g., soy wax). Petroleum-derived paraffinic waxes are particularly prevalent. Non-conventional waxes, particularly Fischer-Tropsch and hydrogenated vegetable waxes, are becoming progressively more important for wax applications. Wax blends may also be used in certain instances.

Waxes of various types are in demand for making items such as, for example, candles, coatings, inks, cosmetics, paints, rubber, electrical components and electronics, plastics, adhesives (e.g., hot melt adhesives), lubricants (e.g., polyvinyl chloride (PVC) extrusion lubricants), surfactants, paper sizings, synthetic drilling fluids, separating agents, food additives, pharmaceutical agents, and many other purposes. There is considerable variability among different types of waxes and wax sources. Consequently, certain wax compositions are better suited for some applications compared to others. Factors that may dictate the suitability of a wax composition for an intended application include, for example, viscosity, density, melting point, congealing point, and burning properties, as well as secondary performance factors influenced by these parameters.

Significant quantities of wax are used in the candle industry, as well as for PVC rheology modification. Waxes are also key components in a wide variety of adhesive products, particularly hot melt adhesives. Hot melt adhesives are thermoplastic polymer systems that are applied to a substrate in a molten state. Hot melt adhesives are configured to flow smoothly onto a surface and then rapidly cool to a tough, adherent solid at room temperature. Thus, viscosity as a function of temperature is a key feature to ensure proper hot melt performance. Increasing bond strength and improving temperature resistance are two properties waxes can impart during this process. Waxes also enable control of the viscosity during processing. Because of their typically low molecular weights and relatively high crystallization temperatures, wax compositions may solidify quickly and with a high degree of crystallinity. Wax compositions having relatively high melting points, e.g., ≥50° C., may be desirable for free standing pillar candles and other applications requiring high mechanical integrity. Container candles and other applications requiring lower mechanical integrity may utilize wax compositions having lower melting points. At present, there are few options for producing high-quality synthetic wax compositions suitable for meeting these needs and others, particularly with tunable melting points to address particular application-specific requirements.

SUMMARY

The present disclosure provides processes for forming wax compositions from linear alpha olefins. The processes comprise: providing an olefinic feed in a reactor, the olefinic feed comprising a first linear alpha olefin having m carbon atoms and a second linear alpha olefin having n carbon atoms, the first linear alpha olefin and the second linear alpha olefin being the same or different, wherein m and n are independently selected integers each ranging from about 12 to about 100, and the olefinic feed optionally comprises one or more internal olefins and/or one or more branched olefins; contacting the olefinic feed with a metal carbene catalyst in the reactor; forming ethylene and a hydrocarbon substance comprising a linear olefin dimer in the reactor, the linear olefin dimer being formed from the first linear alpha olefin and the second linear alpha olefin, the linear olefin dimer comprising two carbon atoms less than a sum of m and n; removing the ethylene from the reactor while forming the linear olefin dimer; and isolating a wax composition comprising the linear olefin dimer, a hydrogenated reaction product thereof, or any combination thereof.

BRIEF DESCRIPTION OF THE DRAWINGS

The following figures are included to illustrate certain aspects of the present disclosure and should not be viewed as exclusive embodiments. The subject matter disclosed is capable of considerable modifications, alterations, combinations, and equivalents in form and function, as will occur to one having ordinary skill in the art and having the benefit of this disclosure.

DETAILED DESCRIPTION

Figure 1:
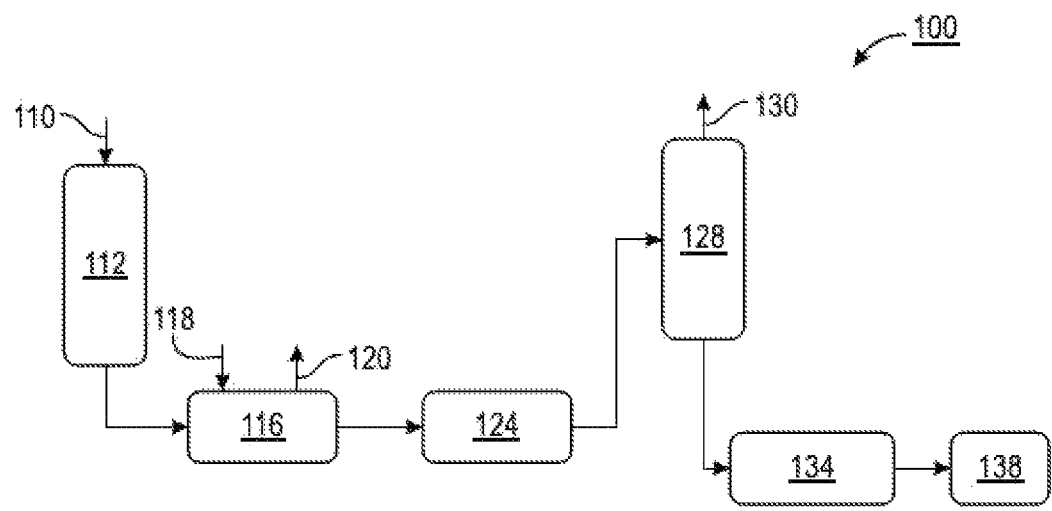
FIG. 1 is a flow diagram of a process for producing wax compositions comprising partially hydrogenated linear olefin dimers.

The present disclosure relates to wax compositions and, more specifically, wax compositions comprising linear olefin dimers and/or hydrogenated linear olefin dimers and methods for production thereof.

As discussed above, there is growing demand for waxes in a variety of industries, especially high-quality waxes, such as those suitable for making candles or hot melt adhesive products, for example. Wax shortages, especially for high-quality waxes, are anticipated over the coming years. At present, there are few synthetic options available for producing high-quality wax compositions, particularly with the ability to tune melting points of the wax compositions to meet particular application-specific needs.

The present disclosure demonstrates that certain abundant products of the chemical and petroleum industries may be suitable precursors for forming high-quality wax compositions and/or blends thereof. More specifically, the present disclosure utilizes linear alpha olefins (LAOS) as a feed for producing linear olefin dimers, which may be further hydrogenated or partially hydrogenated to form the corresponding linear paraffins as a reaction product. As used herein, the term "partially hydrogenated" means that at least some olefinic bonds remain in the reaction product obtained from hydrogenating linear olefin dimers. That is, a mixture of unhydrogenated linear olefin dimers and linear paraffins may be present. The linear olefin dimers, the corresponding linear paraffins formed from the linear olefin dimers, or blends of the linear olefin dimers and linear paraffins, optionally in combination with other reaction products and/or with other blending waxes or additives, may comprise high-quality wax compositions that may be suitable for a variety of applications. Advantageously, the melting points of the wax compositions described herein may be tailored by selecting the chain length of the linear alpha olefins used to form the linear olefin dimers and/or by adjusting the extent of unsaturation present in the wax compositions after hydrogenation, if performed. In general, wax compositions that are fully saturated have the highest melting point for a given carbon chain length, and wax compositions that have had none of their unsaturation removed have the lowest melting point for a given carbon chain length. Blends of linear olefin dimers and linear paraffins produced therefrom may afford a spectrum of accessible melting points between these two extremes. Blends of different linear olefin dimers and/or linear paraffins formed from LAOs having different carbon chain lengths may similarly afford melting point variability in the disclosure herein.

More specifically, a hydrocarbon substance comprising a linear olefin dimer, a hydrogenated or partially hydrogenated reaction product of the linear olefin dimer, or any combination thereof, may provide wax compositions having melting points of about 25° C. or greater, wherein the linear olefin dimers are formed from linear alpha olefins having about 12 carbons or more, such as about 12 carbons to about 100 carbons, more particularly about 12 carbons to about 30 carbons or about 12 carbons to about 26 carbons. Particular feeds used in the disclosure herein may include $C_{12}$-$C_{18}$ LAOS, $C_{20}$-$C_{24}$ LAOS, or $C_{24+}$ LAOS. Optionally, a feed comprising LAOs having about 12 to about 30 carbons may be used in combination with a small amount of a feed comprising $C_{30}$ to $C_{100}$ LAOS. Suitable sources of linear alpha olefins used as a feed for producing linear olefin dimers may include those obtained from ethylene dimerization, alcohol dehydration, renewable LAOs (e.g., biomass-derived hydrocarbon compounds, such as biomass-derived lactones, unsaturated acids, ethanol, or the like), or blends of one or more of such sources, or combination thereof.

Feeds comprising higher linear alpha olefins, such as linear alpha olefins having 18 carbons or more, may have a significant content of internal olefins and/or branched olefins. Metathesis of internal and/or branched olefins in a feed comprising linear alpha olefins may lead to the formation of branched olefin dimers and/or a hydrogenated reaction product thereof, which may also be suitably present in the wax compositions disclosed herein. The melting points of the wax compositions described herein may be adjusted depending upon the extent of unsaturation present and/or the amount of branching present, thereby allowing tailoring to be realized for particular applications.

Still more specifically, the wax compositions of the present disclosure may be formed by reacting at least one linear alpha olefin with a metal carbene catalyst, which may afford formation of the linear olefin dimer by a metathesis reaction and commensurate loss of ethylene. A single linear alpha olefin may self-dimerize to form the linear olefin dimers or two different linear alpha olefins may form asymmetrical linear olefin dimers. Mixtures of linear olefin dimers having different carbon chain lengths may also be formed in this manner. The linear olefin dimers may comprise two carbon atoms less than a total number of carbon atoms in the linear alpha olefins from which they were produced (as a result of ethylene loss). Surprisingly and advantageously, linear olefin dimers may be formed through olefin metathesis in a continuous mode, such as in a continuous stirred tank reactor (CSTR) or a tubular reactor, which may be compatible with continuous production line processes for distilling and/or hydrogenating the linear olefin dimers to afford wax compositions having a desired extent of unsaturation for melting point adjustment. Other suitable reactors for conducting olefin metathesis according to the disclosure herein may include CSTRs or CSTRs in series, stirred tank reactors (STRs) or STRs in series, tubular reactors, staged bubble column reactors, tubular reactors with co-current gas/liquid flows, tubular reactors with periodic gas/liquid separation, and the like. CSTRs may facilitate ready addition and mixing of the catalyst, thus allowing dispersion of the catalyst through the volume of the feed, which may be of high viscosity. The ready catalyst dispersion may be especially advantageous, since the catalyst is often used at a concentration of only a few ppm in the reaction mixture.

All numerical values within the detailed description and the claims herein are modified by "about" or "approximately" with respect to the indicated value, and take into account experimental error and variations that would be expected by a person having ordinary skill in the art. Unless otherwise indicated, ambient temperature (room temperature) is about 25° C.

As used in the present disclosure and claims, the singular forms "a," "an," and "the" include plural forms unless the context clearly dictates otherwise.

The term "and/or" as used in a phrase such as "A and/or B" herein is intended to include "A and B," "A or B," "A," and "B."

For the purposes of the present disclosure, the new numbering scheme for groups of the Periodic Table is used. In said numbering scheme, the groups (columns) are numbered sequentially from left to right from 1 through 18, excluding the f-block elements (lanthanides and actinides). Under this scheme, the term "transition metal" refers to any atom from groups 3-12 of the Periodic Table, inclusive of the lanthanides and actinide elements.

The term "hydrocarbon" refers to a class of compounds containing hydrogen bound to carbon, and encompasses (i) saturated hydrocarbon compounds, (ii) unsaturated hydrocarbon compounds, and (iii) mixtures of hydrocarbon compounds (saturated and/or unsaturated), including mixtures of hydrocarbon compounds having different numbers of carbon atoms. The term "$C_n$," refers to hydrocarbon(s) or a hydrocarbyl group having n carbon atom(s) per molecule or group, wherein n is a positive integer. Such hydrocarbon compounds may be one or more of linear, branched, cyclic, acyclic, saturated, unsaturated, aliphatic, or aromatic.

The terms "hydrocarbyl" and "hydrocarbyl group" are used interchangeably herein. The term "hydrocarbyl group" refers to any $C_1$-$C_{100}$ hydrocarbon group bearing at least one unfilled valence position when removed from a parent compound. Optional heteroatom substitution may be present in a hydrocarbyl group.

The term "alkyl" refers to a hydrocarbyl group having no unsaturated carbon-carbon bonds.

The term "alkenyl" refers to a hydrocarbyl group having a carbon-carbon double bond. The terms "alkene" and "olefin" are used synonymously herein. Similarly, the terms "alkenic" and "olefinic" are used synonymously herein. Unless otherwise noted, all possible geometric isomers are encompassed by these terms.

The term "substituted" refers to replacement of at least one hydrogen atom or carbon atom of a hydrocarbon or hydrocarbyl group with a heteroatom or heteroatom functional group. Heteroatoms may include, but are not limited to, B, O, N, S, P, F, Cl, Br, I, Si, Pb, Ge, Sn, As, Sb, Se, and Te. Heteroatom functional groups that may be present in substituted hydrocarbons or hydrocarbyl groups include, but are not limited to, functional groups such as O, S, S=O, $S(=O)_2$, $NO_2$, F, Cl, Br, I, $NR_2$, OR, SeR, TeR, $PR_2$, $AsR_2$, $SbR_2$, SR, $BR_2$, $SiR_3$, $GeR_3$, $SnR_3$, $PbR_3$, where R is a hydrocarbyl group or H. Suitable hydrocarbyl R groups may include alkyl, alkenyl, alkynyl, aryl, heteroaryl, cycloalkyl, heterocyclyl, and the like, any of which may be optionally substituted.

The term "optionally substituted" means that a hydrocarbon or hydrocarbyl group may be unsubstituted or substituted. For example, the term "optionally substituted hydrocarbyl" refers to replacement of at least one hydrogen atom or carbon atom in a hydrocarbyl group with a heteroatom or heteroatom functional group. Unless otherwise specified, any of the hydrocarbyl groups herein may be optionally substituted.

The terms "linear" and "linear hydrocarbon" refer to a hydrocarbon or hydrocarbyl group having a continuous carbon chain without side chain branching.

The term "linear alpha olefin (LAO)" refers to an alkenic hydrocarbon bearing a carbon-carbon double bond at a terminal (end) carbon atom of the main carbon chain.

The term "internal olefin (IO)" refers to an alkenic hydrocarbon having a carbon-carbon double bond between two internal (non-end) carbon atoms of the main carbon chain.

The terms "branch," "branched" and "branched hydrocarbon" refer to a hydrocarbon or hydrocarbyl group having a linear main carbon chain in which a hydrocarbyl side chain extends from the linear main carbon chain. The term "unbranched" refers to a straight-chain hydrocarbon or hydrocarbyl group.

The term "branched olefin (BO)" refers to an alkenic hydrocarbon having a carbon-carbon double bond at any position and a hydrocarbyl side chain at any position along the main carbon chain.

The terms "self-metathesis" and "self-dimerization" refer to formation of an olefin dimer from two of the same type of olefin molecule.

The term "blend" refers to a mixture of two or more components, such as two or to more LAOs or two or more linear olefin dimers and/or a hydrogenated reaction product thereof.

Accordingly, wax compositions of the present disclosure may comprise a hydrocarbon substance comprising a linear olefin dimer formed from a first linear alpha olefin having m carbon atoms (LAO $C_m$) and a second linear alpha olefin having n carbon atoms (LAO $C_n$), a hydrogenated or partially hydrogenated reaction product of the linear olefin dimer, or any combination thereof. The first linear alpha olefin and the second linear alpha olefin are the same or different, and the linear olefin dimer comprises two carbon atoms less than a sum of m and n. Variables m and n are independently selected integers each ranging from about 12 to about 100, such as from about 12 to about 30 or about 12 to about 26, and m and n may be the same or different. The wax composition may have a melting point of about 25° C. or greater. For some carbon chain lengths and extents of unsaturation, the wax composition may have a melting point of about 60° C. or greater. Optionally, the olefinic feed may comprise linear alpha olefins comprising about 12 to about 30 carbons, along with a minority co-feed comprising linear alpha olefins comprising about 30 to about 100 carbons (e.g., about 5 wt % to about 30 wt %, based on the total weight of the olefinic feed). Olefinic feeds comprising higher linear alpha olefins ($C_{30+}$) may have relatively small amounts of linear alpha olefins (e.g., about 30 wt % or less), with the remainder of the feed comprising branched olefins or internal olefins.

The present disclosure further relates to methods for production of the foregoing wax compositions, as discussed in greater detail herein below. Various uses for the wax compositions are also discussed herein.

The hydrocarbon substance may further comprise one or more branched olefin dimers, a hydrogenated or partially hydrogenated reaction product thereof, or any combination thereof, which is in combination with the linear olefin dimer and/or a linear paraffin formed via hydrogenation of the linear olefin dimer. Internal olefins may also be formed from isomerization of linear alpha olefins under the metathesis reaction conditions and undergo reaction similarly to those already present in the feed. The one or more branched olefin dimers may comprise a dimerized reaction product formed from an internal olefin and the first linear alpha olefin or the second linear alpha olefin, a self-dimerized reaction product formed from the internal olefin, a dimerized reaction product formed from a branched olefin and the first linear alpha or the second linear alpha olefin, a self-dimerized reaction product formed from the branched olefin, a dimerized reaction product formed from the internal olefin and the branched olefin, or any combination thereof. Each of the one or more branched olefin dimers comprises at least two carbon atoms less than a sum of the number of carbon atoms in a first olefin and a second olefin from which the one or more branched olefins were formed. If ethylene is lost during dimerization, the one or more branched olefin dimers have two carbon atoms less than a sum of the number of carbon atoms in the first olefin and the second olefin. Larger carbon fragments may be lost if the double bond undergoing metathesis is an internal olefin or the double bond bears a hydrocarbyl substitution. Because internal olefins and branched olefins undergo metathesis slower than do linear alpha olefins, the one or more branched olefin dimers typically comprise a minor component of the wax compositions disclosed herein. This may be the case, even when the feed comprises a low concentration of linear alpha olefins.

Linear alpha olefins, which also may be referred to as terminal olefins or terminal alkenes, suitable for use in the present disclosure may be isolated from a petroleum refinery stream. Alternatively, linear alpha olefins may be synthesized by several processes starting from low molecular weight feedstock materials, such as via metathesis reaction of ethylene or through byproduct isolation from the Fischer-Tropsch synthesis. Biomass-derived linear alpha olefins and linear alpha olefins from other sources may also be used in the disclosure herein. Linear alpha olefins are composed of a linear hydrocarbon chain, and have a chemical formula of $C_xH_{2x}$ (x is an integer greater than or equal to 2, particularly an even integer greater than or equal to 3 or greater than or equal to 4) with a double bond between C-1 and C-2.

The linear olefin dimers of the present disclosure may be formed by dimerization of the first linear alpha olefin and the second linear alpha olefin in the presence of a metal carbene catalyst. Dimerization may occur through metathesis, wherein a molecule of ethylene is collectively lost from the first linear alpha olefin and the second linear alpha olefin, and the resulting linear olefin dimer possesses two carbon atoms less than a sum of m and n. A linear paraffin formed from the linear olefin dimer as a hydrogenated reaction product similarly has two carbon atoms less than a sum of m and n. Larger carbon fragments may be lost when internal olefins or branched olefins undergo metathesis.

The linear olefin dimers of the present disclosure may have a structure represented by Formula 1

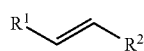

Formula 1 wherein $R^1$ and $R^2$ are independently selected normal alkyl groups having from about 10 to about 98 carbon atoms. In more specific examples, $R^1$ and $R^2$ may be independently selected normal alkyl groups having from about 10 to about 24 carbon atoms or about 10 to about 28 carbon atoms. $R^1$ and $R^2$ may be of the same length or different lengths, resulting from selection of first and second LAOs that are the same or different, respectively.

The wax compositions formed according to the disclosure herein may have a melting point of about 10° C. or greater or about 25° C. or greater. The melting point may vary based upon the number of carbon atoms in the linear olefin dimer and the extent of unsaturation in the wax composition. Wax compositions that are fully unsaturated (substantially all linear olefin dimers hydrogenated to the corresponding paraffins) have higher melting points than that of fully unsaturated olefin dimers. Partially hydrogenating the wax compositions and/or blending a desired proportion of linear olefin dimers and linear paraffins formed from linear olefin dimers may allow tunable, intermediate melting points in between these two extremes to be achieved. Depending on the number of carbon atoms in the first and second linear alpha olefins and the extent of unsaturation, the melting point may be about 25° C. or greater, or about 30° C. or greater, or about 40° C. or greater, or about 60° C. or greater, or about 80° C. or greater, or about 100° C. or greater, or about 120° C. or greater, or about 140° C. or greater. Preferably, the melting point of the wax compositions is about 180° C. or lower. More preferably, the melting point of the wax compositions may range from about 40° C. to about 140° C.

Other physical properties that may be used to characterize the wax compositions disclosed herein include, for example, needle penetration depth and viscosity. The kinematic viscosity (KV) at 100° C. of the wax compositions of the present disclosure may range from about 2 cSt to about 20 cSt, or from about 4 cSt to about 15 cSt, or from about 6 cSt to about 10 cSt, alternately from about 3 cSt to about 10 cSt, or from about 3.5 cSt to about 4 cSt. The foregoing viscosities may be particularly applicable to wax compositions having a melting point of about 100° C. or below; wax compositions having higher melting points may exhibit higher viscosity values. Brookfield viscosity values of about 10 cP to about 300 cP at 125° C. may be realized in some cases.

The wax compositions formed according to the present disclosure may have a total linear olefin dimer and linear paraffin content of about 70 wt % or more, or about 80 wt % or more, or about 90 wt % or more, or about 95 wt % or more, or even 100 wt %, based on the total weight of the wax composition. The linear olefin dimer and linear paraffin content may depend upon the amount of branched olefins and internal olefins present in the feed, wherein feeds comprising significant quantities of these species may afford higher amounts of branched olefin dimers and branched paraffins in the reaction product. For example, when significant quantities of $C_{24+}$ LAOs are used to form the linear olefin dimers, either alone or in combination with one or more lower LAOs ($<C_{24}$), an increased amount of branching may be present, in which case the wax compositions may comprise less than about 70 wt % linear olefin dimers or linear paraffins.

Provided there are not excessive amounts of branched olefins and/or internal olefins in the feed, the wax compositions formed according to the present disclosure may have a total branched olefin dimer and branched paraffin content of about 30 wt % or less, or about 20 wt % or less, or about 10 wt % or less, or about 5 wt % or less, or about 2 wt % or less, or about 1 wt % or less, or about 0.5 wt % or less, or about 0.1 wt % or less, based on the total weight of the wax composition. Wax compositions formed according to the present disclosure from feeds comprising higher amounts of branched and/or internal olefins may have a total branched olefin dimer and branched paraffin content of about 50 wt % to about 70 wt %, based on the total weight of the wax composition.

Petroleum slack wax (slack wax) is a generic term for a byproduct of a petroleum refining process that contains oil and wax. Slack wax is a complex combination of hydrocarbons obtained from a petroleum fraction by solvent crystallization (i.e., dewaxing) or as a distillation fraction from a waxy crude. Slack wax is substantially comprised of saturated straight and branched chain hydrocarbons that predominantly have carbon numbers of about $C_{20}$ or greater. Slack wax is often in abundance where petroleum is processed, so it can be obtained cheaply.

A blending wax may be present in the wax compositions disclosed herein. The blending wax may be used to tailor the properties of the wax compositions. Any amount of the blending wax ranging from about 0.1 wt % to about 99.9 wt % may be present in combination with the linear olefin dimer and/or the hydrogenated reaction product formed therefrom. The blending wax may be a wax formed from a linear olefin dimer and/or hydrogenated reaction product thereof that has a different number of carbon atoms than a primary wax in the wax composition. Alternately, different wax types, such as slack wax, may comprise a blending wax in the wax compositions described herein. Certain wax compositions described herein may comprise slack wax with a free oil content of at least 2 wt %, or at least 3 wt % or at least 5 wt %. The free oil content of the slack wax may be about 35 wt % or less or about 20 wt % or less. Suitable ranges of free oil in slack wax may include 2 wt % to 20 wt %, 10 wt % to 20 wt %, or 3 wt % to 20 wt %. Slack waxes suitable for use in the disclosure herein may have a melting point in a range of about 43° C. to about 66° C., for example from 50° C. to about 53° C. Slack waxes generally can have a color ranging from white to brown.

When used, blending waxes suitable for forming the wax compositions disclosed herein may include, for example, petroleum slack wax, fully refined wax, semi-refined wax, scale wax, stearic acid wax, soft wax and/or foots oil, microcrystalline wax, beeswax, vegetable-based waxes such as soy and palm wax, synthetic waxes such as $C_{20+}$ LAO waxes and Fischer-Tropsch waxes, and various combinations thereof. Other types of blending wax may be suitable as well. The blending wax may have a degree of unsaturation differing from that of the hydrocarbon substance formed by metathesis of the first linear alpha olefin and the second linear alpha olefin.

Linear olefin dimers in the disclosure herein may be synthesized through dimerization of one or more linear alpha olefins, such as $C_{12}$ to $C_{100}$ linear alpha olefins, particularly $C_{12}$ to $C_{30}$ linear alpha olefins or $C_{12}$ to $C_{26}$ linear alpha olefins, in the presence of a metal carbene catalyst. In some instances, an olefinic feed comprising $C_{30+}$ LAOs may be used as a co-feed in combination with a majority olefinic feed comprising $C_{12}$ to $C_{30}$ LAOS. The linear alpha olefins used for forming the linear olefin dimers may be of the same or different chain lengths. In some embodiments, the linear alpha olefins may be predominately of the same chain length. In other embodiments, the linear alpha olefins may comprise a blend of two or more $C_{12}$ to $C_{100}$ linear alpha olefins (or a blend of two or more $C_{12}$ to $C_{30}$ linear alpha olefins or $C_{12}$ to $C_{26}$ linear alpha olefins), particularly linear alpha olefins having an even number of carbon atoms within this range. Such linear olefin dimers may be suitable for forming the wax compositions disclosed herein. Linear olefin dimers of either type may undergo subsequent hydrogenation to form a hydrogenated or partially hydrogenated reaction product thereof, or any combination thereof that may also be suitable for use in the disclosure herein.

Processes of the present disclosure may comprise: providing an olefinic feed in a reactor, the olefinic feed comprising a first linear alpha olefin having m carbon atoms (LAO $C_m$) and a second linear alpha olefin having n carbon atoms (LAO $C_n$), the first linear alpha olefin and the second linear alpha olefin being the same or different, wherein m and n are independently selected integers each ranging from about 12 to about 100, such as from about 12 to about 30 or from about 12 to about 26, and the olefinic feed optionally comprising one or more internal olefins and/or one or more branched olefins; contacting the olefinic feed with a metal carbene catalyst in the reactor; forming ethylene and a hydrocarbon substance comprising a linear olefin dimer in the reactor, the linear olefin dimer being formed from the first linear alpha olefin and the second linear alpha olefin, the linear olefin dimer comprising two carbon atoms less than a sum of m and n; removing the ethylene from the reactor while continuing to form the linear olefin dimer; and isolating a wax composition comprising the linear olefin dimer, a hydrogenated reaction product thereof, or any combination thereof.

Various metal carbene catalysts may be suitable to promote dimerization of linear alpha olefins to form linear olefin dimers according to the disclosure herein. Suitable metal carbene catalysts for forming linear olefin dimers may be transition metal carbene complexes comprising a group 6 or a group 8 transition metal, such as molybdenum, ruthenium, tungsten or osmium, for example. Molybdenum and ruthenium carbene complexes may be particularly suitable for this purpose.

Some metal carbene catalysts suitable for forming linear olefin dimers via metathesis according to the disclosure herein may include, for example, those having a structure represented by Formula 2

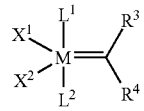

Formula 2 wherein M is a group 8 transition metal (e.g., Os or Ru); $X^1$ and $X^2$ are anionic ligands, wherein $X^1$ and $X^2$ may be the same or different; $R^3$ and $R^4$ are independently selected from the group consisting of hydrogen, hydrocarbyl, substituted hydrocarbyl, heteroatom-containing hydrocarbyl, substituted heteroatom-containing hydrocarbyl, and —$(Z)_n$—Fn where n is zero or 1, Z is a hydrocarbylene, substituted hydrocarbylene and/or heteroatom-containing hydrocarbylene linkage, and Fn is an optional functional group containing a heteroatom; and $L^1$ and $L^2$ are independently selected from any Lewis base ligand. Optionally $R^3$ and/or $R^4$ may be covalently bonded to $L^1$ or $L^2$ to form at least one metallocycle ring. Illustrative examples of such metal carbene catalysts are described further in U.S. Pat. Nos. 7,683,180, 8,846,939, 6,838,489, and 6,613,910, and International Patent Application Publication 00/071554, each of which is incorporated herein by reference in its entirety. Particularly suitable examples include those in which M is Ru, which may be referred to as Grubbs-type catalysts.

$R^3$ and $R^4$ may be independently selected from hydrogen, $C_2$-$C_{20}$ alkenyl, $C_2$-$C_{20}$ alkynyl, $C_1$-$C_{20}$ alkyl, aryl, $C_1$-$C_{20}$ carboxylate, $C_1$-$C_{20}$ alkoxy, $C_2$-$C_{20}$ alkenyloxy, $C_2$-$C_{20}$ alkynyloxy, aryloxy, $C_2$-$C_{20}$ alkoxycarbonyl, $C_1$-$C_{20}$ alkylthio, $C_1$-$C_{20}$ alkylsulfonyl or $C_1$-$C_{20}$ alkylsulfinyl, each optionally substituted with $C_1$-$C_5$ alkyl, halogen, $C_1$-$C_5$ alkoxy or with a phenyl group optionally substituted with halogen, $C_1$-$C_5$ alkyl or $C_1$-$C_5$ alkoxy.

Suitable alkyl groups can include, for example, methyl, ethyl, n-propyl, i-propyl, butyl, pentyl, hexyl, or any isomer thereof. Alkenyl groups can include, for example, 1-propenyl, 2-propenyl; 3-propenyl, butenyl, pentenyl, hexenyl, or any isomer thereof, 1,3-hexadienyl, 2,4,6-heptatrienyl, or cycloalkenyl. Alkenyloxy groups can include, for example, $H_2C=CHCH_2O$, $(CH_3)_2C=CHCH_2O$, $(CH_3)CH=CHCH_2O$, $(CH_3)CH=C(CH_3)CH_2O$, or $CH_2=CHCH_2CH_2O$. Alkynyl groups can include, for example, ethynyl, 1-propynyl, 3-propynyl, butynyl, pentynyl, hexynyl, or any isomer thereof, 2,7-octadiynyl, or 2,5,8-decatriynyl. Alkynyloxy groups can include, for example, $HCCCH_2O$, $CH_3CCCH_2O$, or $CH_3CCCH_2OCH_2O$. Alkylthio groups can include, for example, methylthio, ethylthio, propylthio, butylthio, pentylthio, hexylthio, or any isomers thereof. Alkylsulfonyl groups can include, for example, $CH_3SO_2$, $CH_3CH_2SO_2$, $CH_3CH_2CH_2SO_2$, $(CH_3)_2CHSO_2$, butylsulfonyl, pentylsulfonyl, hexylsulfonyl, or any isomers thereof. Alkylsulfinyl groups can include, for example, $CH_3SO$, $CH_3CH_2SO$, $CH_3CH_2CH_2SO$, $(CH_3)_2CHSO$, butylsulfinyl, pentylsulfinyl, hexylsulfinyl, or any isomers thereof. Carboxylate groups can include, for example, $CH_3CO_2CH_3CH_2CO_2$, $C_6H_5CO_2$, or $(C_6H_5)CH_2CO_2$. Aryl groups can include, for example, phenyl, p-tolyl, or p-fluorophenyl. Alkoxide groups can include, for example, methoxide, ethoxide, t-butoxide, or phenoxide. Diketonates can include, for example, acetylacetonate, or 2,4-hexanedionate. Sulfonate groups can include, for example, trifluoromethanesulfonate, tosylate, or mesylate. Phosphine groups can include, for example, trimethylphosphine, triphenylphosphine, or methyldiphenylphosphine. Phosphite groups can include, for example, trimethylphosphite, triphenylphosphite, or methyldiphenylphosphite. Phosphinite groups can include, for example, triphenylphosphinite, or methyldiphenylphosphinite.

Functional groups, herein, may be referred to as "Fn" such as halo, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{24}$ aryloxy, $C_6$-$C_{24}$ aralkyloxy, $C_6$-$C_{24}$ alkaryloxy, acyl (including $C_2$-$C_{24}$ alkylcarbonyl (—CO-alkyl) and $C_6$-$C_{24}$ arylcarbonyl (—CO-aryl)), acyloxy (—O-acyl, including $C_2$-$C_{24}$ alkylcarbonyloxy (—O—CO-alkyl) and $C_6$-$C_{24}$ arylcarbonyloxy (—O—CO-aryl)), $C_2$-$C_{24}$ alkoxycarbonyl (—(CO)—O-alkyl), $C_6$-$C_{24}$ aryloxycarbonyl (—(CO)—O-aryl), halocarbonyl (—CO)—X where X is halo), $C_2$-$C_{24}$ alkylcarbonato (—O—(CO)—O-alkyl), $C_6$-$C_{24}$ arylcarbonato (—O—(CO)—O-aryl), carboxy (—COOH), carboxylato (—COO—), carbamoyl (—(CO)—NH_2), mono-($C_1$-$C_{24}$ alkyl)-substituted carbamoyl (—(CO)—NH($C_1$-$C_{24}$ alkyl)), di-($C_1$-$C_{24}$ alkyl)-substituted carbamoyl (—(CO)—N($C_1$-$C_{24}$ alkyl)$_2$), mono-($C_1$-$C_{24}$ haloalkyl)-substituted carbamoyl (—(CO)—NH($C_1$-$C_{24}$ haloalkyl)), di-($C_1$-$C_{24}$ haloalkyl)-substituted carbamoyl (—(CO)—N($C_1$-$C_{24}$ haloalkyl)$_2$), mono-($C_5$-$C_{24}$ aryl)-substituted carbamoyl (—(CO)—NH-aryl), di-($C_5$-$C_{24}$ aryl)-substituted carbamoyl (—(CO)—N($C_5$-$C_{24}$ aryl)$_2$), di-N—($C_1$-$C_{24}$ alkyl), N—($C_5$-$C_{24}$ aryl)-substituted carbamoyl (—(CO)—N($C_1$-$C_{24}$ alkyl)($C_5$-$C_{24}$ aryl), thiocarbamoyl (—(CS)—NH$_2$), mono-($C_1$-$C_{24}$ alkyl)-substituted thiocarbamoyl (—(CS)—NH($C_1$-$C_{24}$ alkyl)), di-($C_1$-$C_{24}$ alkyl)-substituted thiocarbamoyl (—(CS)—N($C_1$-$C_{24}$ alkyl)$_2$), mono-($C_5$-$C_{24}$ aryl)-substituted thiocarbamoyl (—(CS)—NH-aryl), di-($C_5$-$C_{24}$ aryl)-substituted thiocarbamoyl (—(CS)—N($C_5$-$C_{24}$ aryl)$_2$), di-N—($C_1$-$C_{24}$ alkyl), N—($C_5$-$C_{24}$ aryl)-substituted thiocarbamoyl (—(CS)—N($C_1$-$C_{24}$ alkyl)($C_5$-$C_{24}$ aryl), carbamido (—NH—(CO)—NH$_2$), cyano (—C≡N), cyanato (—O—C≡N), thiocyanato (—S—C≡N), isocyanate (—N=C=O), thioisocyanate (—N=C=S), formyl (—(CO)—H), thioformyl (—(CS)—H), amino (—NH$_2$), mono-($C_1$-$C_{24}$ alkyl)-substituted amino (—NH($C_1$-$C_{24}$ alkyl), di-($C_1$-$C_{24}$ alkyl)-substituted amino (—N($C_1$-$C_{24}$ alkyl)$_2$), mono-($C_5$-$C_{24}$ aryl)-substituted amino (—NH($C_5$-$C_{24}$ aryl), di-($C_5$-$C_{24}$ aryl)-substituted amino (—N($C_5$-$C_{24}$ aryl)$_2$), $C_2$-$C_{24}$ alkylamido (—NH—(CO)-alkyl), $C_6$-$C_{24}$ arylamido (—NH—(CO)-aryl), imino (—CR=NH where R includes without limitation hydrogen, $C_1$-$C_{24}$ alkyl, $C_5$-$C_{24}$ aryl, $C_6$-$C_{24}$ alkaryl, $C_6$-$C_{24}$ aralkyl, etc.), $C_2$-$C_{20}$ alkylimino (—CR=N(alkyl), where R includes without limitation hydrogen, $C_1$-$C_{24}$ alkyl, $C_5$-$C_{24}$ aryl, $C_6$-$C_{24}$ alkaryl, $C_6$-$C_{24}$ aralkyl, etc.), arylimino (—CR=N(aryl), where R includes without limitation hydrogen, $C_1$-$C_{20}$ alkyl, $C_5$-$C_{24}$ aryl, $C_6$-$C_{24}$ alkaryl, $C_6$-$C_{24}$ aralkyl, etc.), nitro (—NO$_2$), nitroso (—NO), sulfo (—SO$_2$—OH), sulfonato (—SO$_2$—O—), $C_1$-$C_{24}$ alkylsulfanyl (—S-alkyl; also termed "alkylthio"), $C_5$-$C_{24}$ arylsulfanyl (—S-aryl; also termed "arylthio"), $C_1$-$C_{24}$ alkylsulfinyl (—(SO)-alkyl), $C_5$-$C_{24}$ arylsulfinyl (—(SO)-aryl), $C_1$-$C_{24}$ alkylsulfonyl (—SO$_2$-alkyl), $C_1$-$C_{24}$ monoalkylaminosulfonyl (—SO$_2$—N(H) alkyl), $C_1$-$C_{24}$ dialkylaminosulfonyl (—SO$_2$—N(alkyl)$_2$), $C_5$-$C_{24}$ arylsulfonyl (—SO$_2$-aryl), boryl (—BH$_2$), borono (—B(OH)$_2$), boronato (—B(OR)$_2$ where R includes without limitation alkyl or other hydrocarbyl), phosphono (—P(O)(OH)$_2$), phosphonato (—P(O)(O$^-$)$_2$), phosphinato (—P(O)(O—)), phospho (—PO$_2$), and phosphino (—PH$_2$); and the hydrocarbyl moieties $C_1$-$C_{24}$ alkyl (preferably $C_1$-$C_{12}$ alkyl, more preferably $C_1$-$C_6$ alkyl), $C_2$-$C_{24}$ alkenyl (preferably $C_2$-$C_{12}$ alkenyl, more preferably $C_2$-$C_6$ alkenyl), $C_2$-$C_{24}$ alkynyl (preferably $C_2$-$C_{12}$ alkynyl, more preferably $C_2$-$C_6$ alkynyl), $C_5$-$C_{24}$ aryl (preferably $C_5$-$C_{14}$ aryl), $C_6$-$C_{24}$ alkaryl (preferably $C_6$-$C_{16}$ alkaryl), and $C_6$-$C_{24}$ aralkyl (preferably $C_6$-$C_{16}$ aralkyl).

In particular examples, $R^3$ and $R^4$ may be independently vinyl, H, Me, or Ph. $X^1$ and $X^2$ may be independently a halide (e.g., $C_1$, Br, F), $CF_3CO_2$, $CH_3CO_2$, $CFH_2CO_2$, $(CH_3)_3CO$, $(CF_3)_2(CH_3)CO$, $CF_3(CH_3)_2$ CO, PhO, MeO, EtO, tosylate, mesylate, or trifluoromethanesulfonate. In at least one embodiment, $X^1$ and $X^2$ are $C_1$. $L^1$ and $L^2$ may be independently PMe$_3$, P(C$_6$H$_{11}$)$_3$, PPh$_3$, P(p-Tol)$_3$, P(o-Tol)$_3$, PMePh$_2$, PPhMe$_2$, P(CF$_3$)$_3$, P(p-FC$_6$H$_4$)$_3$, pyridine, P(p-CF$_3$C$_6$H$_4$)$_3$, (p-F)pyridine, (p-CF$_3$)pyridine, P(C$_6$H$_4$—SO$_3$Na)$_3$, or P(CH$_2$C$_6$H$_4$—SO$_3$Na)$_3$, substituted or unsubstituted imidazolidines (e.g., 1,3-bis(2,4,6-trimethylphenyl)-2-imidazolidinylidene, 1,3-bis(2,4,6-trimethylphenyl) imidazol-2-ylidene, 1,3-bis(2,6-di-isopropylphenyl)-2-imidazolidinylidene, or 1,3-bis(2,6-di-isopropylphenyl) imidazol-2-ylidene).

A particularly suitable example of a metal carbene catalyst for use in forming the linear olefin dimers disclosed herein may have a structure represented by Formula 3. The metal carbene catalyst represented by Formula 3 may be referred to as Grubbs II catalyst herein.

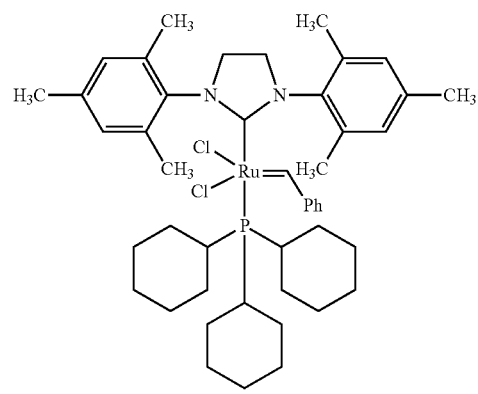

Formula 3

Other metal carbene catalysts that may be suitably used for forming the olefin dimers disclosed herein include, for example, a metal carbene catalyst having a structure represented by Formula 4

Formula 4

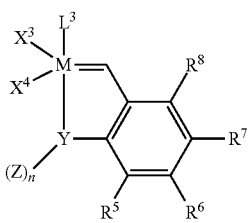

wherein M is a group 8 transition metal (e.g., Os or Ru); $L^3$ is an N-heterocyclic Lewis base ligand; $X^3$ and $X^4$ are halide; Y is a heteroatom selected from N, O, S, or P, such as Y is O or N; $R^5$, $R^6$, $R^7$, and $R^8$ are each independently selected from the group consisting of hydrogen, halogen, alkyl, alkenyl, alkynyl, aryl, heteroalkyl, heteroatom containing alkenyl, heteroalkenyl, heteroaryl, alkoxy, alkenyloxy, aryloxy, alkoxycarbonyl, carbonyl, alkylamino, alkylthio, aminosulfonyl, monoalkylaminosulfonyl, dialkylaminosulfonyl, alkylsulfonyl, nitrile, nitro, alkylsulfinyl, trihaloalkyl, perfluoroalkyl, carboxylic acid, ketone, aldehyde, nitrate, cyano, isocyanate, hydroxyl, ester, ether, amine, imine, amide, halogen-substituted amide, trifluoroamide, sulfide, disulfide, sulfonate, carbamate, silane, siloxane, phosphine, phosphate, borate, or -A-Fn, wherein "A" is a divalent hydrocarbon moiety selected from alkylene and arylalkylene, wherein the alkyl portion of the alkylene and arylalkylene groups can be linear or branched, saturated or unsaturated, cyclic or acyclic, and substituted or unsubstituted, wherein the aryl portion of the of arylalkylene can be substituted or unsubstituted, and wherein heteroatoms and/or functional groups may be present in either the aryl or the alkyl portions of the alkylene and arylalkylene groups, and Fn is a functional group, or together to form a cyclic group, and any combination of Y, Z, $R^5$, $R^6$, $R^7$, and $R^8$ can be linked to form one or more cyclic groups; n is 0, 1, or 2, such that n is 1 for the divalent heteroatoms O or S, and n is 2 for the trivalent heteroatoms N or P; Z is a group selected from hydrogen, alkyl, aryl, functionalized alkyl, functionalized aryl where the functional group(s) may independently be one or more or the following: alkoxy, aryloxy, halogen, carboxylic acid, ketone, aldehyde, nitrate, cyano, isocyanate, hydroxyl, ester, ether, amine, imine, amide, trifluoroamide, sulfide, disulfide, carbamate, silane, siloxane, phosphine, phosphate, or borate; methyl, isopropyl, sec-butyl, t-butyl, neopentyl, benzyl, phenyl or trimethylsilyl. Additionally, R5, R6, R7, R8, and Z may independently be thioisocyanate, cyanato, or thiocyanato.

$L^3$ may be an N-heterocyclic Lewis base ligand selected from the group consisting of 1,3-bis(2,4,6-trimethylphenyl)-2-imidazolidinylidene, 1,3-bis(2,4,6-trimethylphenyl)imidazol-2-ylidene, 1,3-bis(2,6-di-isopropylphenyl)-2-imidazolidinylidene, or 1,3-bis(2,6-di-isopropylphenyl)imidazol-2-ylidene.

A particularly suitable metal carbene catalyst having a structure represented by Formula 5 may be used for forming the linear olefin dimers disclosed herein. The metal carbene catalyst represented by Formula 5 may be referred to as Hoveyda-Grubbs II catalyst herein.

Formula 5

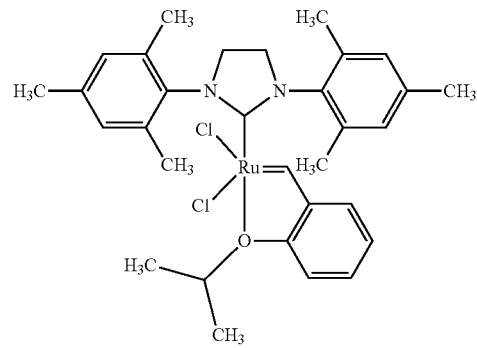

Still other metal carbene catalysts that may be suitably used for forming the linear olefin dimers disclosed herein include, for example, metal carbene catalysts having a structure represented by Formula 6

Formula 6

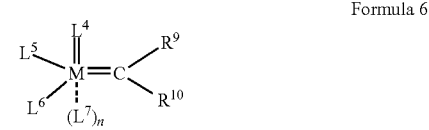

wherein M is a group 6 transition metal atoms (e.g., Mo), $R^9$ and $R^{10}$ are independently a hydrogen atom or a group selected from a substituted or unsubstituted alkyl group having 1 to 12 carbon atoms, a substituted or unsubstituted cycloalkyl group having 3 to 20 carbon atoms, and a substituted or unsubstituted aryl group having 6 to 12 carbon atoms, $L^4$ is an oxygen atom, or a nitrogen atom that is unsubstituted, or substituted with a substituent selected from a substituted or unsubstituted alkyl group having 1 to 12 carbon atoms, a substituted or unsubstituted cycloalkyl group having 3 to 20 carbon atoms and a substituted or unsubstituted aryl group having 6 to 12 carbon atoms, $L^5$ and $L^6$ are independently a substituted or unsubstituted 5 to 15-membered conjugated heterocyclic group that includes at least one nitrogen atom, or a group represented by O—$R^{11}$, wherein $R^{11}$ is a group selected from a substituted or unsubstituted alkyl group having 1 to 12 carbon atoms, a substituted or unsubstituted cycloalkyl group having 3 to 20 carbon atoms, and a substituted or unsubstituted aryl group having 6 to 30 carbon atoms, $L^7$ is a phosphorus-containing ligand, an oxygen-containing ligand, or a nitrogen-containing ligand, and n is 0 or 1.

A particularly suitable example of a metal carbene catalyst useful for forming linear olefin dimers according to the disclosure herein may have a structure represented by Formula 7.

Formula 7

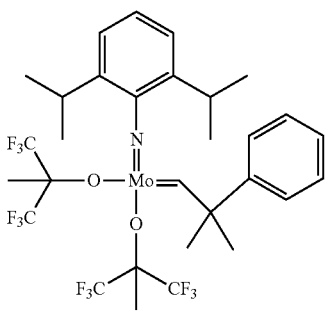

The metal carbene catalyst may be referred to as Schrock catalyst herein.

Still other illustrative metal carbene catalysts that may be suitably used for forming the linear olefin dimers disclosed herein include, for example, those having a structure represented by Formula 8.

Formula 8

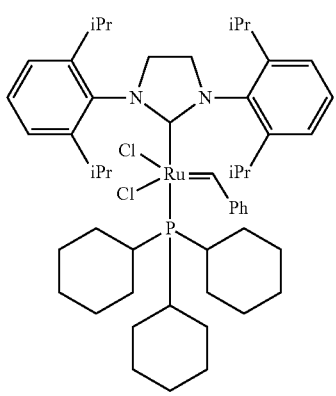

Reaction 1 below illustrates the general structure for a pair of LAOs and their subsequent dimerization to form a linear olefin dimer via metathesis. Subsequent and optional hydrogenation to form the corresponding paraffin, i.e., a hydrogenated reaction product of the linear olefin dimer, is also shown in Reaction 1. Accordingly, for Reaction 1, $R^1$ and $R^2$ are independently selected alkyl groups having from about 10 to about 98 carbon atoms, such as 10 to about 28 or about 10 to about 24 carbon atoms. The $R^1$ and $R^2$ groups in each LAO may be of the same length, or they may be of differing lengths.

Reaction 1

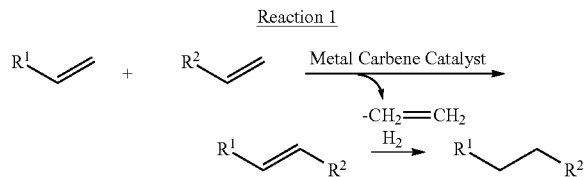

Hydrogenation of the linear olefin dimers described above may be carried out in any suitable manner in a slurry or fixed bed reactor system using a variety of Ni, Pt or Pd hydrogenation catalysts. Suitable hydrogenation conditions, hydrogenation catalysts, reactors and the like will be familiar to one having ordinary skill in the art. Reactors suitable for hydrogenation of the linear olefin dimers include, but are not limited to batch reactors, plug-flow reactors, and liquid continuous mode reactors. When the reactor is a liquid continuous mode reactor, the hydrogenated reaction product may be recycled with a fresh feed of the linear olefin dimers and flashed to carry sufficient hydrogen dissolved therein to perform the hydrogenation reaction. Such system configurations may simplify the reactor design. In some embodiments, residual metal carbene catalysts may serve as a hydrogenation catalyst, in which case addition of a separate hydrogenation catalyst may not be required.

Methods for forming wax compositions of the present disclosure may comprise forming one or more branched olefin dimers, a hydrogenated or partially hydrogenated reaction product thereof, or any combination thereof. The one or more branched olefin dimers may comprise a dimerized reaction product formed from the one or more internal olefins and the first or the second linear alpha olefin, a self-dimerized reaction product of the one or more internal olefins, a dimerized reaction product formed from the one or more branched olefins and the first or the second linear alpha olefin, a self-dimerized reaction product of the one or more branched olefins, a dimerized reaction product formed from the one or more internal olefins and the one or more branched olefins, or any combination thereof. Each of the one or more branched olefin dimers may comprise at least two carbon atoms less than a sum of the number of carbon atoms in a first olefin and a second olefin from which the one or more branched olefins may be formed.

Processes of the present disclosure may further comprise purifying the olefinic feed to remove one or more contaminants therefrom. Purification may mitigate the presence of one or more contaminants therein (e.g., oxygenates, moisture, metals, heteroatoms, and any combination thereof), particularly during metal carbene catalyst preforming of a metathesis process (e.g., dimerization). Purifying may comprise contacting the feed with an adsorbent, sparging the feed with an inert gas, or any combination thereof in the same or different location(s), and purifying the linear olefin dimer(s) from light species and unreacted feed by distillation/flashing and/or falling-film evaporation, thereby limiting the quantity of contaminants returned to the metathesis reaction upon recycling the feed.

Purification of the olefinic feed may comprise contacting the olefinic feed with an adsorbent, and/or sparging the feed with an inert gas, or any combination thereof to form a purified olefinic feed. Optionally, purification of the olefinic feed may also involve contacting the olefinic feed in a melt phase with an adsorbent for removal of the one or more contaminants.

Purification of the reaction product, which may be subjected to further metathesis, may further comprise removing the spent catalyst from the reaction product through a column packed with a solid adsorbent (e.g., silica gel).

Suitable examples of adsorbents for the removal of the one or more contaminants may include zeolite molecular sieves, modified activated aluminas, mixtures thereof, and non-regenerable metal oxide/sulfide products. Adsorbent selection may depend on the specific impurities to be removed and the olefinic feed in which they are contained. To ensure optimal performance of the adsorbent, the adsorbent is suitably activated. Activation of the adsorbent, may be carried out with an inert gas (e.g., $N_2$) at a temperature of about 200° C. to about 300° C. (or from about 220° C. to about 280° C., or from about 240° C. to about 260° C.), and/or for a period of time of about 2 hours (or about 4 hours, or about 6 hours, or about 8 hours, or about 10 hours, or about 12 hours, or about 24 hours). AZ-300 adsorbent, for example, a homogenous combination of modified activated alumina and molecular sieve adsorbents, may afford complementary performance characteristics of both materials. AZ-300 adsorbent has high capacity for light acid gases and a broad range of polar molecules. Though AZ-300 adsorbent contains zeolite, it does not typically require a preload step when processing unsaturated streams. The elimination of the preload process, while retaining the effective removal of polar compounds, provides a time-efficient process. The purification process may also include sparging of the olefinic feed with a stream of inert gas (e.g., Ar or $N_2$) to remove oxygen.

Suitable olefinic feeds described herein are not considered to be particularly limited. In some process configurations, olefinic feed may comprise one or more $C_{12}$ to $C_{100}$ linear alpha olefins, particularly one or more $C_{12}$ to $C_{30}$ linear alpha olefins, optionally in further combination with one or more $C_{30}$-$C_{100}$ linear alpha olefins. Suitable linear alpha olefins may include, but are not limited to $C_{12+}$ linear alpha olefins, $C_{14+}$ linear alpha olefins, $C_{16+}$ linear alpha olefins, $C_{18+}$ linear alpha olefins, $C_{20+}$ linear alpha olefins, $C_{24+}$ linear alpha olefins, or $C_{26+}$ linear alpha olefins, such as 1-dodecene, 1-tridecene, 1-tetradecene, 1-pentadecene, 1-hexadecene, 1-heptadecene, 1-octadecene, 1-nonadecene, 1-eicosene, 1-heneicosene, 1-docosene, 1-tricosene, 1-tetracosene, 1-pentacosene, 1-hexacosene, 1-heptacosene, 1-octacosene, 1-nonacosene, 1-triacontene, or any mixture thereof. Internal olefins, branched olefins, and the like may also comprise at least a portion of the olefinic feed in various process implementations. Internal olefins and/or branched olefins may undergo metathesis in combination with linear alpha olefins in some process configurations. For example, the olefinic feed may comprise about 25 wt % to about 100 wt % linear alpha olefins or about 70 wt % to about 100 wt % linear alpha olefins, 0 wt % to 75 wt % or 0 wt % about 30 wt % internal olefins, and 0 wt % to 75 wt % or about 0 wt % to about 30 wt % branched olefins, based on a total weight of the olefinic feed. In another example, the olefinic feed may comprise 85 wt % to 100 wt % of linear alpha olefins, 0 wt % to 15 wt % of internal olefins, and 0 wt % to 15 wt % of branched olefins, based on a total weight of the olefinic feed. Any amount specifying 0 wt % is inclusive of non-zero amounts of a specified component.

The purified olefinic feed may be further transferred to another reactor for further processing by olefin metathesis. Alternately, the olefinic feed may undergo metathesis in the same reactor in which it was purified.

The metathesis processes of the present disclosure may be carried out in a continuous mode or in batch reactors, such as stirred-batch reactors, via a batch or semi-batch production mode. Surprisingly and advantageously, the wax compositions of the present disclosure may be prepared in a continuous production mode, at any conventional plant equipped with various process equipment such as continuous stirred-tank reactors (CSTRs), stirred-tank reactors equipped with an online catalyst injection mechanism, and/or tubulars reactor, stirred batch reactors, separators, condensers, compressors, and the like. For example, suitable reactors for the formation of linear olefin dimers of the present disclosure may include CSTR or CSTRs in series, STR or STRs in series, tubular reactors, staged bubble column reactors, tubular reactors with co-current gas/liquid flow, tubular reactors with periodic gas/liquid separation, the like, or any combination thereof. Preferably, the metathesis reaction may be carried out in a CSTR, since such reactors may achieve ready catalyst dispersion of the low-abundance catalyst. One of ordinary skill in the art will be familiar with such equipment and be able to utilize the same for carrying out the methods disclosed herein. Hence, methods for forming wax compositions of the present disclosure may comprise: forming the linear olefin dimer in a continuous mode, wherein the linear olefin dimer has a structure represented by Formula 1. Such methods of the present disclosure provide wax compositions in good to excellent yield, such as 40 wt % to 100 wt %, or 45 wt % to 95 wt %, or 50 wt % to 90 wt %, wherein about 30% to about 100% of the olefinic feed is converted into ethylene and linear olefin dimers.

Purified olefinic feed may pass from a purification reactor to a reactor (i.e., metathesis reactor), such as a CSTR or CSTRs in series, a STR or STRs in series, a tubular reactor, a staged bubble column reactor, a tubular reactor with co-current gas/liquid flow, a tubular reactor with periodic gas/liquid separation, the like, or any combination thereof, wherein the metal carbene catalyst may be provided as a solid or as a solution in paraffinic wax or unreactive liquid hydrocarbon solvents, such as toluene. For example, suitable solvents can be aromatic solvents (e.g., toluene) or a paraffinic solvent (e.g., cyclohexane, Isopar™ M). Thus, in at least one embodiment, the metal carbene catalyst may be provided as a homogeneous catalyst solution. Metal carbene catalysts may also be suitably provided in suspension using, for example, a hydrogenated linear olefin dimer (e.g., a $C_{24}$-$C_{60}$ hydrogenated linear olefin dimer), a low viscosity polyalphaolefin (PAO), and/or a combination thereof. A low viscosity PAO may have a viscosity of about 10 centistokes (cSt) or less (or 8 cSt or less, or 6 cSt or less, or 4 cSt or less, or 2 cSt or less) at 100° C. as measured by ASTM method D445.

Alternately, the metathesis reaction of the olefinic feed may be carried out using heterogeneous catalysts. In that case, the metathesis reaction may be carried out in a fixed-bed reactor.

Olefin metathesis (e.g., dimerization) may be carried out under inert atmosphere (e.g., Ar or $N_2$) and/or partial vacuum, by contacting the olefinic feed with the metal carbene catalyst described above under conditions effective to form a hydrocarbon substance comprising at least one linear olefin dimer having a structure represented by Formula 1. Examples of suitable metal carbene catalysts may include those comprising a group 6 or 8 transition metal, such as the metal carbene catalysts described above and represented by Formulas 2 to 7. Suitable reaction temperatures during metathesis may range from about room temperature to about 200° C. (i.e., about 25° C. to about 200° C.), or any subrange in between. More desirably, the metal carbene catalyst may be contacted with the olefinic feed at a temperature of about 60° C. to about 80° C., for example. In at least one embodiment, the reaction temperature may be about 65° C. Pressure conditions may be chosen to maintain the olefinic feed in a liquid state during the metathesis reaction.

The metal carbene catalyst may be contacted with the olefinic feed at a metal carbene catalyst concentration of about 10 ppm or less, or about 8 ppm or less, or about 6 ppm or less, or about 4 ppm or less, or about 3 ppm or less, or about 2.8 ppm or less, or about 2.6 ppm or less, or about 2.4 ppm or less, or about 2.2 ppm or less, or about 2 ppm or less, or about 1.8 ppm or less, or about 1.6 ppm or less, or about 1.4 ppm or less, or about 1.2 ppm or less, or about 1 ppm or less, based on the transition metal atom therein. Loading of the metal carbene catalyst in the metathesis reactor may range from about 0.0005 mol. % to about 0.02 mol. %, or about 0.001 mol. % to about 0.01 mol. %, or about 0.0025 mol. % to 0.008 mol. %.

Since the metathesis reaction is reversible, formation of linear olefin dimers may be promoted by removing the ethylene produced during the metathesis reaction. Removing the ethylene may drive the reaction equilibrium toward linear olefin dimer products. For instance, during the metathesis reaction, concurrent stripping and removal of ethylene gas may be performed. Ethylene stripping may be conducted using a stream of inert gas, sparging the reaction products with inert gas, or applying a partial vacuum. Conversion of the LAOs to linear olefin dimers may range from about 30% to 100% conversion, or about 40% to 100% conversion, or about 50% to 100% conversion, or about 60% to 100% conversion, or about 70% to 100% conversion.

In some instances, the olefinic feed and the metal carbene catalyst may be contacted in a hydrocarbon solvent inert to undergoing olefin metathesis, such as to maintain a liquid phase during the metathesis reaction (e.g., when employing higher LAOS, such as $C_{20+}$ LAOs or $C_{24+}$ LAOs). Examples of suitable inert hydrocarbon solvents may include, but are not limited to, aromatic and alkylaromatic solvents (e.g., benzene, naphthalene, toluene, and xylenes), paraffinic solvents, or any combination thereof. Use of an inert hydrocarbon solvent may be beneficial if the olefinic feed or the linear olefin dimer formed therefrom is a solid under the reaction conditions.

During the metathesis reaction, deactivated metal carbene catalyst and metal carbene catalyst debris can act as poisons toward the fresh catalyst. Continuous metathesis reaction conditions may alleviate this difficulty to some degree. Optionally, the spent catalyst (e.g., transition metals, ligands, or any combination thereof) can be removed from the reaction product through a column packed with a solid adsorbent such as, but not limited to, activated carbon and oxides (e.g., alumina, silica), or through liquid-liquid extraction. The spent catalyst may be further deactivated by using a quenching treatment comprising a vinyl halide or vinyl ether (e.g., ethyl vinyl ether), for example. Optionally, the spent catalyst can be further removed by filtration using a diatomaceous earth (e.g., CELITE®). As discussed further below, however, spent (deactivated) metal carbene catalyst (if not removed) may advantageously be used to promote hydrogenation or partial hydrogenation to form an at least partially paraffinic hydrocarbon substance.

The linear olefin dimers may be subjected to a purification process before and/or after hydrogenation. Accordingly, the linear olefin dimer or a linear paraffin formed therefrom can be recovered in pure or near-pure form, such as about >95% purity, or about >97% purity, or about >99% purity, or about >99.5% purity. Conventional distillation or falling-film evaporation may be suitable for this purpose.

When distillation of the linear olefin dimers occurs before hydrogenation, doping with chemical stabilizers may be conducted to preclude metathesis or polymerization of the olefinic group. For example, butylated hydroxytoluene (BHT) is an antioxidant which can be used as a chemical stabilizer herein, such as at a concentration of about 50 ppm to about 100 ppm, for example.

In some embodiments, the wax compositions described herein may be at least partially hydrogenated (e.g., by hydrogenating at least a portion of the olefinic groups in a linear olefin dimer), such as to afford a desired melting point of the wax compositions. Such processes of the present disclosure may further comprise: contacting the linear olefin dimer with a hydrogenation catalyst under hydrogenation reaction conditions; and hydrogenating at least a portion of the linear olefin dimer to form a linear paraffin product. In at least one embodiment, the linear olefin dimer may be fully hydrogenated. Alternately, the linear olefin dimer may be partially hydrogenated, wherein the wax composition comprises a mixture of linear olefin dimers and linear paraffins formed therefrom.

As discussed above, hydrogenation may be carried out before and/or after distillation of the linear olefin dimer to provide an at least partially paraffinic wax composition. Hydrogenation may be carried out in a slurry or fixed-bed reactor unit packed with a catalyst suitable for hydrogenation processes (e.g., nickel, platinum, or palladium on carbon or an oxide support). Preferably, hydrogenation may be carried out in a slurry or fixed-bed reactor unit. Alternately, spent metal carbene catalyst may be used to promote hydrogenation in some instances. The extent of unsaturation in the wax composition may be tuned to provide a desired melting point, for example. In a given wax composition, the extent of unsaturation may be about 5% or greater, or about 10% or greater, or about 15% or greater, or about 20% or greater, or about 25% or greater, or about 50% or greater, or about 75% or greater, or about 90% or greater, or fully hydrogenated (100% hydrogenation). Following hydrogenation, the resulting linear paraffins may be further distilled, if desired. Blending of linear olefin dimers and linear paraffins may also occur after distillation as well.

Spent metal carbene catalyst may be used to promote hydrogenation in some instances. When spent metal carbene catalyst functions as a hydrogenation catalyst, the hydrogenation reaction may be carried out at high temperatures of about 80° C. or more, such as from about 80° C. to about 350° C., or about 80° C. to about 250° C., or from about 100° C. to about 200° C., or from about 120° C. to about 250° C., and/or a pressure of about 2 gauge bar (barg) to about 100 barg, or about 5 barg to about 80 barg, or about 10 barg to about 60 barg, or about 20 barg to about 50 barg. When using fresh metal carbene catalyst, the hydrogenation reaction may be carried out at temperatures of about 80° C. or more, such as from about 80° C. to about 250° C., or from about 100° C. to about 200° C., for example, and/or a pressure of about 5 barg to about 30 barg, or about 10 barg to about 20 barg, for example.

When spent metal carbene catalyst (e.g., Ru catalyst) functions as a hydrogenation catalyst, hydrogenation may be carried out at hydrogenation catalyst loading of about 0.01 wt % to about 3 wt %, or about 0.05 wt % to about 2.5 wt %, or about 0.1 wt % to about 2 wt %, or about 0.2 wt % to about 1.5 wt %, or about 0.3 wt % to about 1 wt %.

When fresh hydrogenation catalyst (e.g., Pt, Pd, and Ru catalysts) is used, hydrogenation may be carried out at hydrogenation catalyst loading of about 0.01 wt % to about 3 wt %, or about 0.05 wt % to about 2.5 wt %, or about 0.1 wt % to about 2 wt %, or about 0.2 wt % to about 1.5 wt %, or about 0.3 wt % to about 1 wt %. When the hydrogenation catalyst is a Ni-based catalyst, hydrogenation may be carried out at hydrogenation catalyst loading of about 50 wt % or more, such as 60 wt % or more, such as 70 wt % or more.

Hydrogenation may be carried out at a temperature of about 80° C. to about 350° C., or about 80° C. to about 250° C., or about 100° C. to about 300° C., or about 200° C. to about 250° C., and/or at a pressure of about 2 gauge bar (barg) to about 100 barg, or about 5 barg to about 80 barg, or about 10 barg to about 60 barg, and/or at a linear olefin dimer/$H_2$ ratio of about 0.2 or greater, or about 1 or greater, or about 2 or greater, or about 3 or greater, or about 4 or greater, or about 5 or greater. In at least one embodiment, hydrogenation is performed at an $H_2$:linear olefin dimer molar ratio of about 2.

Other hydrogenation conditions that may be used to promote full or partial hydrogenation may include, for example, a temperature of about 80° C. to about 250° C., or about 100° C. to about 150° C., and pressure ranging from about 20 barg to about 50 barg.

Hydrogenation may be carried out at a weight hourly space velocity (WHSV) of 2 $h^{-1}$ or less, or 1.5 $h^{-1}$ or less, or 1 $h^{-1}$ or less, or 0.5 $h^{-1}$ or less. Alternately, hydrogenation may be carried out at a WHSV of 0.1 $h^{-1}$ or greater, such as a WHSV of 0.1 $h^{-1}$ to 15 $h^{-1}$, or 0.5 $h^{-1}$ to 12 $h^{-1}$, or 1 $h^{-1}$ to 10 $h^{-1}$. Partial hydrogenation may be realized at a WHSV of about 5 $h^{-1}$ to about 7 $h^{-1}$. The foregoing values refer to that of the liquid feed, excluding hydrogen.

After hydrogenation, when the spent metal carbene catalyst is used as the hydrogenation catalyst, the spent metal carbene catalyst may be further deactivated by using a quenching treatment comprising a vinyl halide or vinyl ether (e.g., ethyl vinyl ether), for example.

After hydrogenation, the hydrogenation catalyst may be removed by filtration using diatomaceous earth (e.g., CELITE® HyFlo filter aid) or a similar filter aid. The hydrogenation catalyst removal can also be performed via suitable techniques such as adsorption on solid adsorbents or liquid-liquid extraction.

Hydrogenation may be accomplished using one or multiple columns set up in sequential order. Due to the exothermic nature of the hydrogenation reaction when using a hydrogenation catalyst (e.g., Ni-based hydrogenation catalyst), the temperature between the entrance and exit of the column may rise from about 40° C. to about 200° C. (or from about 40° C. to about 150° C., or from about 40° C. to about 100° C., or from about 40° C. to about 60° C.). Hydrogenation can be monitored/evaluated by measuring the amount of unsaturates present in the reaction mixture, which may be assayed using a bromine index test method (ASTM method D2710). The bromine index (BI) refers to the number of mg of bromine ($Br_2$) bound by 100 g of sample.

When distillation of the linear olefin dimers occurs before hydrogenation, a portion of the reaction product produced by metathesis can be separated for further blending with the linear paraffins obtained following hydrogenation. That is, the processes of the present disclosure may include blending linear olefin dimers with linear paraffins to afford a desired extent of unsaturation in the wax compositions, wherein an at least partially paraffinic hydrocarbon substance may be present. Alternately, the hydrogenation reaction may be conducted to as to intentionally leave a portion of the linear olefin dimers unhydrogenated. Furthermore, the wax compositions may be further modified through blending with other olefinic or paraffinic blend stock(s), or with one or more blending waxes, which may have a different degree of unsaturation.

The processes of the present disclosure are discussed further hereinafter with reference to FIGS. 1-4.

FIG. 1 is a flow diagram of a process for producing wax compositions comprising partially hydrogenated linear olefin dimers. Process 100 may include purification 112 of feed 110 by introducing feed 110 comprising at least one linear alpha olefin into a reactor, optionally in combination with one or more internal olefins and/or one or more branched olefins, and removing one or more contaminants therefrom. Removal of the one or more contaminants may be carried out by contacting the olefinic feed 110 with an adsorbent, sparging feed 110 with an inert gas, or any combination thereof. The one or more contaminants may comprise a contaminant selected from the group consisting of oxygenates, moisture, metals, heteroatoms, and any combination thereof. In some instances, purification 112 may involve contacting feed 110 in the melt phase with an adsorbent, as described in further detail above.

Purified olefinic feed passes from purification 112 to metathesis reactor 116 containing online catalyst injection mechanism 118, such as a CSTR reactor, CSTRs in series, a STR or STRs in series, a tubular reactor, a staged bubble column reactor, a tubular reactor with co-current gas/liquid flow, a tubular reactor with periodic gas/liquid separation, the like, or any combination thereof, wherein the metal carbene catalyst may be formulated as a solution in paraffinic wax or a paraffinic hydrocarbon, for example. Optionally, the reaction taking place in metathesis reactor 116 may occur in an inert hydrocarbon solvent.

Metathesis in reactor 116 may be carried out under inert atmosphere (e.g., Ar or $N_2$) and/or (partial) vacuum by contacting the purified olefinic feed with the metal carbene catalyst under conditions effective to form at least one linear olefin dimer. The pressure may be adjusted to maintain the reaction mixture in a liquid phase. The ethylene formed during metathesis, as well as any other gaseous byproducts formed therefrom, may be removed via conduit 120 by purging metathesis reactor 116 with an inert gas (e.g., $N_2$) or partial vacuum.

At least one linear olefin dimer may be conveyed to catalyst removal 124, wherein the spent metathesis catalyst (e.g., metals, ligands) can be removed through a column packed with a solid adsorbent such as, but not limited to, activated carbon and oxides (e.g., alumina, silica). For example, the spent catalyst may be removed by filtration using diatomaceous earth (e.g., CELITE®) or a similar filter aid. Furthermore, after hydrogenation mediated by a spent metathesis catalyst, the spent metathesis catalyst may be further deactivated by using a quenching treatment comprising a vinyl halide or vinyl ether (e.g., ethyl vinyl ether), for example. Spent metathesis catalyst removal can be performed via suitable techniques, such as adsorption on solid adsorbents or liquid-liquid extraction (e.g., by using water soluble phosphines). Another alternative for spent metathesis catalyst removal can include the use of the hydrogenation reactor as an adsorbent bed to promote removal of the metathesis catalyst.

At least one linear olefin dimer free of spent catalyst can then be transferred from catalyst removal 124 to separator 128, such as a distillation column, wherein the linear olefin dimer can be further purified. After distillation, unconverted feed 130 may be recovered and recycled, if desired. Distilled linear olefin dimer may be removed for further processing into a linear paraffin, or mixture of linear olefin dimers and linear paraffins in hydrogenation reactor 134. After separation of the hydrogenation catalyst, product 138 may be obtained as a fully or partially hydrogenated wax composition.

Common reference characters are used in the remaining FIGs. to describe elements having a similar function to those shown in FIG. 1. In the interest of brevity, such features are not described in detail again.

Figure 2:
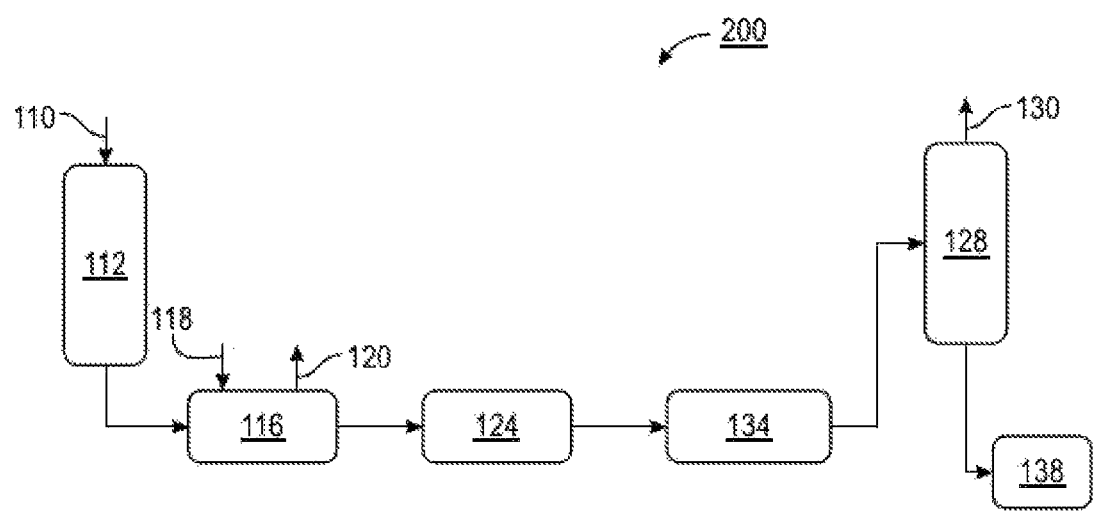
FIG. 2 is a flow diagram of a first variant of a process for producing wax compositions comprising linear paraffins formed from hydrogenated linear olefin dimers.

FIG. 2 is a flow diagram of a first variant of a process for producing wax compositions comprising linear paraffins formed from hydrogenated linear olefin dimers. In process 200, hydrogenation reactor 134 is moved upstream of separator 128, thereby providing substantially linear paraffins for distillation. Product 138 obtained after distillation may comprise substantially linear paraffins.

Figure 3:
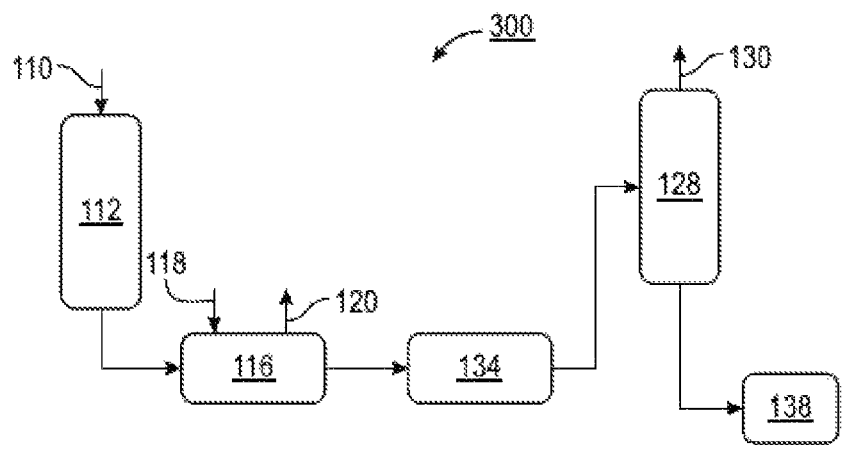
FIG. 3 is a flow diagram of a second variant of a process for producing wax compositions comprising linear paraffins formed from hydrogenated linear olefin dimers.

FIG. 3 is a flow diagram of a second variant of a process with no catalyst removal for producing wax compositions comprising linear paraffins formed from hydrogenated linear olefin dimers. Process 300 in FIG. 3 differs from process 200 in FIG. 2 in that catalyst removal 124 is omitted prior to hydrogenation. In this process configuration, the spent metal carbene catalyst may serve as the hydrogenation catalyst, if desired.

Figure 4:
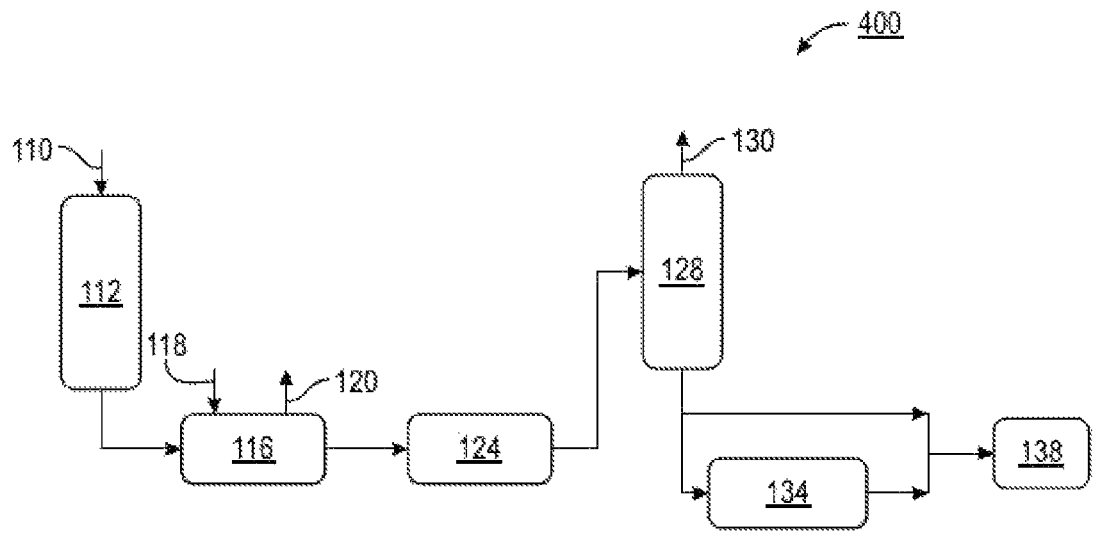
FIG. 4 is a flow diagram of a process for producing wax compositions comprising a blend of linear olefin dimers and linear paraffins formed from hydrogenated linear olefin dimers.

FIG. 4 is a flow diagram of a process for producing wax compositions comprising a blend of linear olefin dimers and linear paraffins formed from hydrogenated linear olefin dimers. In process 400, linear olefin dimers are produced upstream as in process 100 in FIG. 1. Instead of subjecting the entirety of the linear olefin dimers to hydrogenation 134, process 400 subjects a first portion of the linear olefin dimers to hydrogenation 134 and combines the resulting linear paraffins with a second portion of the linear olefin dimers that have not undergone hydrogenation 134. Blending may be conducted to afford a desired extent of unsaturation in product 134. Hydrogenation 134 may be full or partial in the configuration of process 400.

Wax compositions of the present disclosure may comprise a linear olefin dimer and/or a hydrogenated reaction product of the linear olefin dimer in any combination. The wax compositions may be suitable for use in various products such as, for example, candles, cosmetics, rubber, hot melt adhesives, lubricants, pharmaceutical agents, and other articles in which waxes may be used. For instance, high temperature properties of hot melt adhesives may be largely controlled by the melt range and the type of wax being used. Accordingly, the wax compositions of the present disclosure may provide the desirable properties for hot melt adhesive formulations due to their tunable melting point. Candles of various types may also be fabricated using the wax compositions disclosed herein.

Hot melt adhesives may comprise additional components for adjusting the performance and processing properties. Suitable hot melt adhesives formed from a wax composition of the present disclosure may further comprise a thermoplastic polymer or copolymer, and a tackifier resin, examples of which will be known to a person having ordinary skill in the art. The hot melt adhesives may further include an antioxidant, filler or UV stabilizer or a pigment and others additives suitable for the formulation of the desired hot melt adhesives. Wax compositions of the present disclosure may be used as an ingredient in a variety of hot melt adhesive formulations, including, for example, packaging and hygiene hot melt adhesive formulations, wherein the wax compositions may enhance the hot melt adhesive properties, such as, for example, crystallinity kinetics, flow and substrate wetting of the overall hot melt adhesive formulation.

Wax compositions of the present disclosure may also be used as an ingredient in PVC lubrication, including, for example, rigid PVC pipe and profile formulations where the wax compositions can be used as lubricants. Suitable processing aids formed from a wax composition of the present disclosure may further comprise a metal complex that provide heat stability, additional internal/external lubricants, a pigment and optionally a filler, examples of which will be known to a person having ordinary skill in the art.

Wax compositions of the present disclosure may also be used as an ingredient in the tire manufacturing, including, for example, synthetic and natural rubber formulations where the wax compositions can be used as an ozone protecting barrier (i.e., anti-ozone waxes).

Candles formed from wax compositions of the present disclosure may comprise a wick, a wax composition of the present disclosure and an optional blending wax. The wax composition and the optional blending wax may be used to define a body of the candle. The wick of the candle extends from the wax composition defining the body of the candle. The candles may also include a fragrance or scent. Fragrances and scents may be an artificial fragrance and/or a scent derived from natural sources. The fragrance or scent may be an essential oil, such as an oil derived from oranges, eucalyptus, peppermint, lavender, or cedarwood, for example, or any combination thereof. The wax composition and the optional blending wax may also be used as additive and/or colorants. Wax compositions of the present disclosure may be used for manufacturing tealights, votives, and wax melts.

The candles described herein may be formed into a variety of shapes, including, but not limited to, pillar candles and those situated within a container. Pillar candles are freestanding and, in some embodiments, may be formed using wax compositions formed from higher LAO dimers, such as dimers formed from $C_{20+}$ LAOS. Pillar candles may comprise wax compositions of the present disclosure, wherein the wax compositions may have a melting point of about 50° C. or greater. Taper candles may also be suitably formed by the disclosure herein.

The wick(s) used in the candles may be one or more of hemp-core cotton, zinc-core cotton, coreless cotton, cotton with paper filaments, flat-braided wick, wooden wick, or a wick having a paper core, or any other suitable wick known to one having ordinary skill in the art. In some embodiments, the wick may be a high-melting point wick, such as a square braid wick, an ECO wick, a hemp-core wick or a coreless cotton wick.

Other suitable techniques for forming candles using the wax compositions disclosed herein include, for example, extrusion, compression and slurry processing. Suitable extrusion processes may include, for example, screw, hydraulic ram and rotary drum extrusion, in which the wax compositions are squeezed through a suitably sized orifice and then cut to length. In compression processes, the wax compositions may be poured into a mold, and the finished candle may be ejected from the mold following solidification. Slurry processes comprise slurrying air or another gas with the wax compositions and forming a candle, thereby utilizing less of the wax compositions than in other types of processes.

Dyes or other colorants may be included in the candles in a suitable amount to afford an aesthetically pleasing candle. Suitable amounts of dyes or other colorants will be familiar to one having ordinary skill in the art. Other additives that may be suitably included in the candles disclosed herein include, for example, UV stabilizers, antioxidants, polyethylene waxes, microwaxes, mineral oil, stearic acid or other fatty acids, and any combination thereof.

Embodiments disclosed herein include:

A. Processes for making wax compositions. The processes comprise: providing an olefinic feed in a reactor, the olefinic feed comprising a first linear alpha olefin having m carbon atoms and a second linear alpha olefin having n carbon atoms, the first linear alpha olefin and the second linear alpha olefin being the same or different, wherein m and n are independently selected integers each ranging from about 12 to about 100, and the olefinic feed optionally comprises one or more internal olefins and/or one or more branched olefins; contacting the olefinic feed with a metal carbene catalyst in the reactor; forming ethylene and a hydrocarbon substance comprising a linear olefin dimer in the reactor, the linear olefin dimer being formed from the first linear alpha olefin and the second linear alpha olefin, the linear olefin dimer comprising two carbon atoms less than a sum of m and n; removing the ethylene from the reactor while forming the linear olefin dimer; and isolating a wax composition comprising the linear olefin dimer, a hydrogenated reaction product thereof, or any combination thereof.

Embodiment A may have one or more of the following additional elements in any combination:

Element 1: wherein the process further comprises purifying the olefinic feed to remove one or more contaminants therefrom.

Element 2: wherein purifying comprises contacting the olefinic feed with an adsorbent, sparging the feed with an inert gas, or any combination thereof.

Element 3: wherein the one or more contaminants comprise a substance selected from the group consisting of oxygenates, moisture, metals, heteroatoms, and any combination thereof.

Element 4: wherein the metal carbene catalyst is provided as a solution in a paraffinic wax or a paraffinic hydrocarbon solvent.

Element 5: wherein the metal carbene catalyst is a homogeneous catalyst.

Element 6: wherein the metal carbene catalyst is contacted with the olefinic feed at a temperature of about 60° C. to about 75° C.

Element 7: wherein the metal carbene catalyst is contacted with the olefinic feed at a concentration of about 10 ppm or less.

Element 8: wherein the linear olefin dimer comprises two carbon atoms less than a sum of m and n.

Element 9: wherein about 30% to about 100% of the olefinic feed is converted into ethylene and the linear olefin dimer.

Element 10: wherein the process further comprises contacting the linear olefin dimer with a hydrogenation catalyst under hydrogenation reaction conditions; and hydrogenating at least a portion of the linear olefin dimer to form a linear paraffin product.

Element 11: wherein the process further comprises hydrogenating at least a portion of the linear olefin dimer in the presence of the metal carbene catalyst.

Element 12: wherein the linear olefin dimer is fully hydrogenated.

Element 13: wherein the wax composition further comprises: one or more branched olefin dimers, a hydrogenated or partially hydrogenated reaction product thereof, or any combination thereof; wherein the one or more branched olefin dimers comprise a dimerized reaction product formed from the one or more internal olefins and the first linear alpha olefin or the second linear alpha olefin, a self-dimerized reaction product of the one or more internal olefins, a dimerized reaction product formed from the one or more branched olefins and the first linear alpha or the second linear alpha olefin, a self-dimerized reaction product of the one or more branched olefins, a dimerized reaction product formed from the one or more internal olefins and the one or more branched olefins, or any combination thereof; and wherein each of the one or more branched olefin dimers comprises at least two carbon atoms less than a sum of the number of carbon atoms in a first olefin and a second olefin from which the one or more branched olefin dimers were formed.

Element 14: wherein the olefinic feed comprises 70 wt % to 100 wt % of linear alpha olefins, 0 wt % to 30 wt % of internal olefins, and 0 wt % to 30 wt % of branched olefins, based on a total weight of the olefinic feed.

Element 15: wherein olefinic feed comprises 85 wt % to 100 wt % of linear alpha olefins, 0 wt % to 15 wt % of internal olefins, and 0 wt % to 15 wt % of branched olefins, based on a total weight of the olefinic feed.

Element 16: wherein forming the linear olefin dimer is carried out in a continuous mode.

Element 17: wherein the linear olefin dimer has a structure represented by

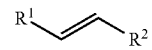

wherein $R^1$ and $R^2$ are independently selected alkyl groups having from about 10 to about 98 carbon atoms.

Element 18: wherein $R^1$ and $R^2$ are independently selected alkyl groups having from about 10 to about 24 carbon atoms or from about 10 to about 28 carbon atoms.

Element 19: wherein m and n are independently selected integers each ranging from about 12 to about 30.

Element 20: wherein the process further comprises separating the linear olefin dimer, the hydrogenated reaction product thereof, or any combination thereof by distillation.

Element 21: wherein the process further comprises after distillation, combining a portion of the linear olefin dimer and a portion of the hydrogenated reaction product thereof to form the wax composition as a blend.

Element 22: wherein the wax composition has a melting point of about 25° C. or greater.

Element 23: wherein the wax composition has a melting point of about 60° C. or greater.

Element 24: wherein the olefinic feed and the metal carbene catalyst are contacted in a hydrocarbon solvent inert to undergoing olefin metathesis.

By way of non-limiting example, illustrative combinations applicable to A include, but are not limited to, 1 and 2; 1-3; 1 and 5; 1 and 6; 1 and 8; 1 and 9; 1 and 10; 1 and 13; 1, 10 and 11; 1 and 10-12; 1 and 16; 1 and 17; 1, 17 and 19; 1 and 20; 1, 20 and 21; 1, and 22 or 23; 1 and 24; 4 and 6; 5 and 6; 5-7; 5 and 8; 5 and 9; 5 and 10; 5, 10 and 11; 5 and 10-12; 5 and 13; 5 and 16; 5 and 17; 5, 17 and 18; 5, 17 and 19; 5 and 20; 5, 20 and 21; 5, and 22 or 23; 5 and 24; 6 and 7; 6 and 8; 6 and 9; 6 and 10; 6, 10 and 11; 6 and 10-12; 6 and 13; 6 and 16; 6 and 17; 6, 17 and 18; 6, 17 and 19; 6 and 20; 6, 20 and 21; 6, and 22 or 23; 6 and 24; 10 and 11; 10-12; 10 and 13; 10 and 16; 10 and 17; 10, 17 and 18; 10, 17 and 19; 10 and 20; 10, 20 and 21; 10, and 22 or 23; 10 and 24; 13 and 14; 13 and 15; 13 and 17; 13, 17 and 18; 13, 17 and 19; 13 and 20; 13, 20 and 21; 13, and 22 or 23; 13 and 24; 17 and 18; 17-19; 17 and 19; 17 and 20; 17, 20 and 21; 17, and 22 or 23; 17 and 24; 20 and 21; and 20, 21, and 22 or 23.

To facilitate a better understanding of the embodiments of the present disclosure, the following examples of preferred or representative embodiments are given. In no way should the following examples be read to limit, or to define, the scope of the invention.

Examples

LAO feeds comprising commercial $C_{14}$, $C_{16}$, $C_{18}$, or $C_{26+}$ LAOs or blends of $C_{12}$-$C_{18}$, $C_{16}$-$C_{18}$, or $C_{20}$-$C_{24}$ LAOs were reacted using a continuous polymerization unit. A 1 gallon continuous stirred-tank reactor (CSTR) made of SS316 low carbon stainless steel was used as the metathesis reactor. Prior to use, the reactor was thoroughly flushed and cleaned with dewatered toluene and then flushed with purified LAOS. The reactor was subsequently passivated with hot toluene at about 95° C. by circulating the hot toluene through the system for about 4 to 5 hours. The LAO feeds were degassed inline using vacuum to remove any remaining dissolved gasses. Unless indicated below, dimerization was conducted under continuous processing conditions. Batch reaction conditions were employed as an alternative where indicated below.

Commercial LAOs typically contain a mixture of alpha olefins, branched olefins, internal olefins, saturates, and other impurities, some of which may remain in the feed even after purification, which potentially can reduce the activity of the catalyst. Accordingly, prior to the metathesis process, the LAO feeds were purified by passage through a hybrid adsorbent bed of AZ-300 molecular sieves adsorbent (Honeywell—UOP) for impurity removal (e.g., sulfur, oxygen, ethylene, peroxides, and other heteroatoms). The AZ-300 was pre-activated with $N_2$ at 250° C. for about 8 hours prior to use.

Olefin metathesis was conducted in the presence of a metal carbene catalyst. Metal carbene catalysts having structures represented by Formulas 3, 5, 7, and 8 were used for the metathesis reactions in the examples below. The metal carbene catalyst having a structure represented by Formula 3 is Grubbs Catalyst™ 2nd Generation (Gr II) (MW=849 g/mol) having two N-2,4,6-trimethylphenyl (N-Mes) groups. The metal carbene catalyst having a structure represented by Formula 5 is Hoveyda-Grubbs Catalyst™ 2nd Generation (HGr II) (MW=627 g/mol) having two N-Mes groups. The metal carbene catalyst having a structure represented by Formula 7 is a Mo-Schrock catalyst (MW=549 g/mol). The metal carbene catalyst having a structure represented by Formula 8 is Grubbs Catalyst™ 2nd Generation Gr II (MW=933 g/mol) having two N-2,6-diisopropylphenyl (N-DIPP) groups.

The metal carbene catalysts were used either in solution (previously dissolved in toluene), as a dry powder, or as a slurry mixed with SPECTRASYN™ 4, a polyalphaolefin synthetic basestock (ExxonMobil Chemicals), also referred to as a Group IV base oil according to the API Base Oil Classification system, without any prior activation process. Homogeneous catalyst solutions were prepared in a glove box under $N_2$ at room temperature by dissolving the metal carbene catalyst (initially in a powder form) in purified, dewatered toluene. The catalyst solutions were protected from moisture and stored at about 4° C. in a refrigerator. Catalyst suspensions/slurries were also prepared using, for example, the metal carbene catalyst powder dispersed in a low viscosity polyalphaolefin (e.g., viscosity of 2-10 cSt, such as 2, 4 or 6 cSt), or a hydrogenated olefin dimer, such as, for example, a hydrogenated $C_{26}$ dimer (prepared from a $C_{14}$ LAO via a metathesis reaction according to the disclosure herein, followed by hydrogenation). Aromatic solvents, such as toluene, may be excluded from the reaction by using a polyalphaolefin catalyst dispersant.

The catalyst solution in toluene was delivered sub-surface to the CSTR reactor via a dip tube using a dedicated metering pump. The catalyst solution was stirred continuously in a separate vessel prior to delivery. In order to achieve a thorough and uniform catalyst distribution through a reactor volume of 1 gallon, stirring of the reaction mixture was conducted at a rate of about 380 rpm. Reactions were conducted at temperature of about 60° C. to about 75° C. at a pressure of about 10-25 psi. The reaction temperature was usually limited to about 60° C. to about 65° C. to limit double bond migration, which may lead to branching in the olefin dimers in addition to that provided by branched or internal olefins in the olefinic feed. At higher temperatures (above 65° C.), and at a residence time of about 2 hours or greater, increased isomerization was observed, which reduced the melting point of the finished product. The reaction system was equilibrated for about 4-6 hours after changes to the process conditions or feed composition before samples were recovered.

Ethylene produced during the metathesis reaction was removed from the CSTR reactor while continuing to form the linear olefin dimer. Ethylene removal was accomplished with $N_2$ sparging at a rate of about 2-3 L/min. Any remaining transition metal residues (e.g., Ru residue) and catalyst debris present in the finished product were removed using silica, CELITE®, or other filtration media. Unconverted monomers and other light products were removed by distillation of the reactor effluent to afford purified linear olefin dimers. Unless otherwise indicated, the distilled product was slurry hydrogenated to obtain the final product using the following hydrogenation conditions: 0.5 wt % Ni powder catalyst, temperature=230° C., pressure=300 psig (20.68 barg) and 1-2 hours of contact time. After hydrogenation, the Ni catalyst was removed using a cellulose fiber FIBRA-CEL® BH-40 and CELITE® HYFLO filter aid. The cellulose fiber FIBRA-CEL® BH-40 was added to the bulk of the fluid to be filtered at a loading of about 0.1 wt % to about 0.5 wt % to promote effective filter cake formation. Alternately, wherein indicated, the hydrogenation may be conducted in a plug-flow reactor using heterogeneous Ni or Pt catalysis, or in a batch autoclave reactor using heterogeneous Pd on carbon catalysis. The temperature and pressure conditions for the plug flow and autoclave reactor reactions were as follows: 20 barg to 50 barg and 120° C. to 250° C.

Example 1: $C_{16}$ LAO Metathesis. The catalyst system was a homogeneous solution of Gr II catalyst (Formula 3) in toluene at a loading of 0.0007 mol % or 0.001 mol %. Commercial $C_{16}$ LAO feed containing about 90 wt % $C_{16}$ LAO, about 3 wt % IOs, and about 7 wt % BOs, was treated with AZ-300 adsorbent and reacted under the general conditions specified above. The reaction was conducted under continuous process conditions. The resulting dimer was further purified by distillation to >99.5% purity. The purified dimer was then hydrogenated using Ni catalyst and filtered. The unhydrogenated dimer had a melting point of about 38° C., and the hydrogenated dimer had a melting point of about 57° C.

Example 2: $C_{16}$ LAO metathesis. The catalyst system was a homogeneous solution of Gr II catalyst (Formula 3) in toluene at a loading of 0.0013 mol %. Commercial $C_{16}$ LAO feed containing about 90 wt % $C_{16}$ LAO, about 3 wt % IOs, and about 7 wt % BOs, was treated with AZ-300 adsorbent and reacted under the general conditions specified above. The reaction was conducted under continuous process conditions. The resulting dimer was further purified by distillation to >99.5% purity. The purified dimer was then hydrogenated using Ni catalyst and filtered. The unhydrogenated dimer had a melting point of about 36° C., and the hydrogenated dimer had a melting point of about 55° C.

Example 3: $C_{18}$ LAO metathesis. The catalyst system was a homogeneous solution of Gr II catalyst (Formula 3) in toluene at a loading of 0.0006 mol %. Commercial $C_{18}$ LAO feed containing about 89 wt % $C_{18}$ LAOS, about 3 wt % IOs, and about 7 wt % BOs was treated with AZ-300 adsorbent and reacted under the general conditions described above. The reaction was conducted under continuous process conditions. The resulting dimer was further purified by distillation to >99.5% purity. The purified dimer was then hydrogenated using Ni catalyst and filtered. The unhydrogenated dimer had a melting point of about 42° C., and the hydrogenated dimer had a melting point of about 65° C.

Example 4: Metathesis of a Blend Comprising $C_{16}$ LAO and $C_{18}$ LAO. The catalyst system was a homogeneous solution of Gr II catalyst (Formula 3) in toluene at a loading of 0.006 mol. %. A blend of commercial $C_{16}/C_{18}$ (1:1 wt./wt.) LAOs containing about 90 wt % $C_{16}/C_{18}$ LAOS, about 3 wt % IOs, and about 7 wt % BOs was treated with AZ-300 adsorbent and reacted under the general conditions specified above. The reaction was conducted under continuous process conditions. The resulting dimer was further purified by distillation to >99.5% purity. The purified dimer was then hydrogenated using Ni catalyst and filtered. The unhydrogenated dimer had a melting point of about 40° C., and the hydrogenated dimer had a melting point of about 61° C.

Table 1 summarizes the continuous process conditions and results obtained for Examples 1-4. Conversion is determined with respect to the LAO content of the feed.

TABLE 1

| Process Conditions | Example 1 | | | | Example 2 | | |
|---|---|---|---|---|---|---|---|
| | Sample 1 | Sample 2 | Sample 3 | Sample 4 | Sample 5 | Sample 6 | Sample 7 |
| Time to reach steady state (hours) | 6 | 6 | 6 | 6 | 6 | 6 | 6 |
| Catalyst Concentration (mol. %) | 0.0007 | 0.0007 | 0.0007 | 0.001 | 0.0013 | 0.0013 | 0.0013 |
| Residence Time (hours) | 1.5 | 2.0 | 4.0 | 2.0 | 1.5 | 2.0 | 4.0 |
| Temperature (° C.) | 65 | 65 | 65 | 65 | 65 | 65 | 65 |
| Conversion (%) | 41 | 48 | 58 | 67 | 57 | 66 | 72 |
| Yield (wt %) | 44 | 55 | 63 | 71 | 61 | 73 | 78 |

| Process Conditions | Example 3 | | | | Example 4 | | |
|---|---|---|---|---|---|---|---|
| | Sample 8 | Sample 9 | Sample 10 | Sample 11 | Sample 12 | Sample 13 | Sample 14 |
| Time to line out (time to reach steady state) (hours) | 6 | 6 | 6 | 6 | 6 | 6 | 6 |
| Catalyst Concentration (mol %) | 0.0006 | 0.0006 | 0.0006 | 0.0006 | 0.0006 | 0.0006 | 0.0006 |
| Residence Time (hours) | 1.5 | 2.0 | 4.0 | 4.0 | 1.5 | 2.0 | 4.0 |
| Temperature (° C.) | 65 | 65 | 65 | 70 | 65 | 65 | 65 |
| Conversion (%) | 48 | 57 | 69 | 74 | 46 | 56 | 67 |
| Yield (wt %) | 51 | 63 | 77 | 82 | 50 | 63 | 75 |

Example 5: Metathesis of a Blend Comprising $C_{18}$, $C_{20}$, $C_{22}$, and $C_{24}$ LAOs. The catalyst system was a homogeneous solution of Gr II catalyst (Formula 3) in toluene. A blend of commercial $C_{18}/C_{20}/C_{22}/C_{24}$ LAOs containing about 6 wt % $C_{18}$ LAOS, 47 wt % $C_{20}$ LAOS, about 33 wt % $C_{22}$ LAOS, and about 14 wt % $C_{24}$ LAOS, each based on total LAOs in the feed, was reacted under the general conditions specified above in batch mode. Overall, the feed contained about 89% $C_{18}/C_{20}/C_{22}/C_{24}$ LAOS, about 2 wt % IOs, and about 9 wt % BOs. The feed was treated with AZ-300 adsorbent. About 150 mL purified $C_{18}/C_{20}/C_{22}/C_{24}$ LAO blend was heated up to 65° C. while stirring. The reaction was conducted in two steps. A first portion of the Gr II (Formula 3) catalyst solution (about 20 μL) was added to the feed to obtain a catalyst loading of 0.0001 mol. %. A stream of $N_2$ was bubbled through the reaction mixture to remove the ethylene produced. The reaction time was about 3 hours. About 37% conversion into the corresponding dimer resulted. A second portion of the catalyst (about 10 μL) was then added to provide a total catalyst loading of 0.0015 mol. %. After about 1 hour, about 48% conversion into the corresponding dimer was obtained. Ethyl vinyl ether (1 drop) was added to quench the catalyst. A total of 105 g of white solid was produced. Upon completion of the metathesis reaction, the catalyst residue was filtered from the reactor effluent using CELITE® diatomaceous earth filter aid. The resulting dimer was further purified by distillation to >99.5% purity. The purified dimer was then hydrogenated using Pt on alumina catalyst at 200° C. and filtered. The unhydrogenated dimer had a melting point of about 57° C., and the hydrogenated dimer had a melting point of about 75° C.

Example 6: Metathesis of a Blend Comprising $C_{18}$, $C_{20}$, $C_{22}$, and $C_{24}$ LAOs. The catalyst system was either a homogeneous solution of Gr II catalyst (Formula 3) in toluene or a powder form of the catalyst. A blend of commercial $C_{18}/C_{20}/C_{22}/C_{24}$ LAOs LAOs containing 6 wt % $C_{18}$ LAOS, 47 wt % $C_{20}$ LAOS, about 33 wt % $C_{22}$ LAOS, and about 14 wt % $C_{24}$ LAOS, each based on total LAOs in the feed, was reacted under the general conditions specified above in batch mode. Overall, the feed contained about 85% LAOS, about 2 wt % IOs, and about 9 wt % BOs. The feed was treated with AZ-300 adsorbent. About 150 mL of purified $C_{18}/C_{20}/C_{22}/C_{24}$ LAOs blend was heated up to 55° C. while stirring. The reaction was conducted in multiple steps. A first portion of solid Gr II (Formula 3) catalyst (about 3 mg) was added as a powder to the feed to obtain a catalyst loading of 0.0005 mol. %. A stream of $N_2$ was bubbled through the reaction mixture to remove the ethylene produced. The solid product started precipitating in 2 hours. The temperature of the reaction was increased to 65° C. After additional stirring for 12 hours the conversion was about 78%. An additional portion of the solid catalyst was added (3 mg) and the temperature was increased to 75° C. After 3 hours the conversion was measured at 90%. Additional Gr II catalyst (5 mg) was added to provide a total catalyst loading of 0.0018 mol. %. After about 2 hours, about 96% conversion into the corresponding dimer was obtained. The hot reaction mixture was filtered through a silica plug to give 96 g of the product. The resulting dimer was further purified by distillation to >99.5% purity. The purified dimer was then hydrogenated using Ni catalyst and filtered. The unhydrogenated dimer had a melting point of about 56° C., and the hydrogenated dimer had a melting point of about 77° C.

Example 7: $C_{14}$ LAO Metathesis. The catalyst system was either a homogeneous solution of Gr II catalyst (Formula 3) in toluene or a powder form of the catalyst. Commercial $C_{14}$ LAO feed containing about 91.5 wt % $C_{14}$ LAOS, about 1.5 wt % IOs, and about 5.5 wt % BOs was treated with AZ-300 adsorbent and reacted under the general conditions specified above in batch mode. About 250 mL of purified $C_{14}$ LAO were heated up to 55° C. while stirring. The reaction was conducted in two steps. A first portion of solid Gr II (Formula 3) catalyst (about 4.2 mg) was added as a powder to the feed to obtain a catalyst loading of 0.0005 mol. %. A stream of $N_2$ was bubbled through the reaction mixture to remove the ethylene produced. After 3 hours the conversion was estimated at 81%. Addition of a second portion of the catalyst (4.2 mg) and stirring for 12 hours at 55° C. resulted in a conversion of 99%. The hot mixture was filtered through a short silica plug to give 137.5 g of a white crystalline material. The unhydrogenated linear olefin dimer had a melting point of about 30° C.

Example 8: Metathesis of a Blend Comprising $C_{12}$, $C_{14}$, $C_{16}$, and $C_{18}$ LAOS. The catalyst system Gr II catalyst (Formula 3) was added to the feed as a powder. A blend of commercial $C_{12}/C_{14}/C_{16}/C_{18}$ LAOs containing about 36 wt % $C_{12}$ LAOS, about 29 wt % $C_{14}$ LAOS, about 21 wt % $C_{16}$ LAOS, and about 14 wt % $C_{18}$ LAOs was reacted under the general conditions specified above in batch mode. The feed was treated with AZ-300 adsorbent, and purged with a stream of nitrogen. About 0.5 kg of neat feed (0.65 L) was heated to 55° C. while stirring. Solid Gr II catalyst (Formula 3) (23 mg) was added to provide a catalyst loading of 0.0011 mol. %, and nitrogen was bubbled through the reaction mixture for 3 hours. An additional portion of the catalyst was then added (23 mg) to provide a final catalyst loading of 0.0022 mol. %, and the mixture was stirred for an additional 12 hours at 55° C. The reaction mixture was filtered through a short plug of silica to provide 366 g of a colorless liquid, which then crystallized at room temperature. $^1$H NMR showed that the LAO conversion was about 100%. The unhydrogenated dimer had a melting point of about 28° C., and the hydrogenated dimer had a melting point of about 50° C.

Example 9: $C_{24+}$ LAO Metathesis. The catalyst system was a dry powder of Grubbs Catalyst™ 2nd Generation Gr II DIPP (Formula 8). A $C_{24+}$ cut was obtained from LAOs produced via ethylene polymerization. The feed was treated with AZ-300 adsorbent, purged with a stream of nitrogen, and was reacted under the general conditions specified above in batch mode. The feed (10 g) was suspended in 200 mL of toluene and the resulting mixture was passed through a fine (N4) filter to give a clear, colorless solution. The solution was then sparged with nitrogen, and stored overnight over a bed of AZ-300 molecular sieves. The catalyst (0.5 mg) was added to the solution at 55° C. to provide a catalyst concentration of 0.0023 mol. %. After stirring for 2 days at 55° C., the solvent was evaporated and a white solid product was dried in vacuum to obtain 7.5 g of dimerized product. The dimerized product was sparingly soluble in benzene and toluene. The unhydrogenated dimer had a melting point of about 80° C., and the hydrogenated dimer had a melting point of about 88° C.

Overall, both Gr II catalyst (Formula 3) and HGr II catalyst (Formula 5) exhibited very high productivity. The turnover numbers (TON) for Gr II and HGr II catalysts were up to 580,000 $s^{-1}$ and 630,000 $s^{-1}$, respectively. The Mo-Schrock catalyst (Formula 7), in contrast, demonstrated significantly lower performance/productivity. When conducting continuous polymerization, the catalyst activity was significantly reduced after about 1.5 to 2.5 hours of reaction. Thus, when the reactor residence time was about 2 hours or greater, no additional deactivation of the catalyst present in the reactor effluent was required.

All documents described herein are incorporated by reference herein for purposes of all jurisdictions where such practice is allowed, including any priority documents and/or testing procedures to the extent they are not inconsistent with this text. As is apparent from the foregoing general description and the specific embodiments, while forms of the disclosure have been illustrated and described, various modifications can be made without departing from the spirit and scope of the disclosure. Accordingly, it is not intended that the disclosure be limited thereby. For example, the compositions described herein may be free of any component, or composition not expressly recited or disclosed herein. Any method may lack any step not recited or disclosed herein. Likewise, the term "comprising" is considered synonymous with the term "including." Whenever a method, composition, element or group of elements is preceded with the transitional phrase "comprising," it is understood that we also contemplate the same composition or group of elements with transitional phrases "consisting essentially of," "consisting of," "selected from the group of consisting of," or "is" preceding the recitation of the composition, element, or elements and vice versa.

Unless otherwise indicated, all numbers expressing quantities of ingredients, properties such as molecular weight, reaction conditions, and so forth used in the present specification and associated claims are to be understood as being modified in all instances by the term "about." Accordingly, unless indicated to the contrary, the numerical parameters set forth in the following specification and attached claims are approximations that may vary depending upon the desired properties sought to be obtained by the embodiments of the present invention. At the very least, and not as an attempt to limit the application of the doctrine of equivalents to the scope of the claim, each numerical parameter should at least be construed in light of the number of reported significant digits and by applying ordinary rounding techniques.

Whenever a numerical range with a lower limit and an upper limit is disclosed, any number and any included range falling within the range is specifically disclosed, including the lower limit and upper limit. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces.

One or more illustrative embodiments are presented herein. Not all features of a physical implementation are described or shown in this application for the sake of clarity. It is understood that in the development of a physical embodiment of the present disclosure, numerous implementation-specific decisions must be made to achieve the developer's goals, such as compliance with system-related, business-related, government-related and other constraints, which vary by implementation and from time to time. While a developer's efforts might be time-consuming, such efforts would be, nevertheless, a routine undertaking for one of ordinary skill in the art and having benefit of this disclosure.

Therefore, the present disclosure is well adapted to attain the ends and advantages mentioned as well as those that are inherent therein. The particular embodiments disclosed above are illustrative only, as the present disclosure may be modified and practiced in different but equivalent manners apparent to one having ordinary skill in the art and having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present disclosure. The embodiments illustratively disclosed herein suitably may be practiced in the absence of any element that is not specifically disclosed herein and/or any optional element disclosed herein.

What is claimed is:

1. A process comprising:
providing an olefinic feed in a reactor, the olefinic feed comprising a first linear alpha olefin having m carbon atoms and a second linear alpha olefin having n carbon atoms, the first linear alpha olefin and the second linear alpha olefin being the same or different, wherein m and n are independently selected integers each ranging from 12 to 30, and the olefinic feed comprises 85 weight percent (wt %) to 100 wt % of linear alpha olefins, 0 wt % to 15 wt % of internal olefins, 0 wt % to 15 wt % of branched olefins, or a combination thereof, based on the olefinic feed;
contacting the olefinic feed with a metal carbene catalyst in the reactor in a continuous production mode, at a temperature of 60° C. to 75° C. and the metal carbene catalyst is contacted with the olefinic feed at a concentration of 10 ppm or less of the metal carbine catalyst;
forming ethylene and a hydrocarbon substance comprising a linear olefin dimer in the reactor in the continuous production mode, the linear olefin dimer being formed from the first linear alpha olefin and the second linear alpha olefin, the linear olefin dimer comprising two carbon atoms less than a sum of m and n;
removing the ethylene from the reactor while forming the linear olefin dimer;
contacting the linear olefin dimer with a hydrogenation catalyst under hydrogenation reaction conditions, and hydrogenating at least a portion of the linear olefin dimer to form a linear paraffin product, optionally in a presence of the metal carbene catalyst; and
isolating a wax composition comprising the linear olefin dimer, a hydrogenated reaction product thereof, or any combination thereof.

2. The process of claim 1, further comprising:
purifying the olefinic feed to remove one or more contaminants therefrom,
wherein purifying comprises contacting the olefinic feed with an adsorbent, sparging the feed with an inert gas, or any combination thereof, and
wherein the one or more contaminants comprise a substance selected from the group consisting of oxygenates, moisture, metals, heteroatoms, and any combination thereof.

3. The process of claim 1, wherein the metal carbene catalyst is provided as a solution in a paraffinic wax or a paraffinic hydrocarbon solvent.

4. The process of claim 1, wherein the metal carbene catalyst is a homogeneous catalyst.

5. The process of claim 1, wherein the metal carbene catalyst is contacted with the olefinic feed at a temperature of 60° C. to 75° C.

6. The process of claim 1, wherein 30% to 100% of the olefinic feed is converted into ethylene and the linear olefin dimer.

7. The process of claim 1, wherein the linear olefin dimer is fully hydrogenated.

8. The process of claim 1, wherein the wax composition further comprises:
one or more branched olefin dimers, a hydrogenated or partially hydrogenated reaction product thereof, or any combination thereof;
wherein the one or more branched olefin dimers comprise a dimerized reaction product formed from the internal olefins and the first linear alpha olefin or the second linear alpha olefin, a self-dimerized reaction product of the internal olefins, a dimerized reaction product formed from the branched olefins and the first linear alpha or the second linear alpha olefin, a self-dimerized reaction product of the branched olefins, a dimerized reaction product formed from the internal olefins and the branched olefins, or any combination thereof; and
wherein each of the one or more branched olefin dimers comprises at least two carbon atoms less than a sum of the number of carbon atoms in a first olefin and a second olefin from which the one or more branched olefin dimers were formed.

9. The process of claim 1, wherein the linear olefin dimer has a structure represented by

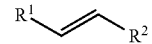

wherein $R^1$ and $R^2$ are independently selected alkyl groups having from 10 to 28 carbon atoms.

10. The process of claim 9, wherein $R^1$ and $R^2$ are independently selected alkyl groups having from 10 to 24 carbon atoms or from 10 to 28 carbon atoms.

11. The process of claim 1, wherein m and n are independently selected integers each ranging from 12 to 30.

12. The process of claim 1, further comprising:
separating the linear olefin dimer, the hydrogenated reaction product thereof, or any combination thereof by distillation; and
after distillation, combining a portion of the linear olefin dimer and a portion of the hydrogenated reaction product thereof to form the wax composition as a blend.

13. The process of claim 1, wherein the wax composition has a melting point of 25° C. or greater.

14. The process of claim 1, wherein the wax composition has a melting point of 60° C. or greater.

15. The process of claim 1, wherein the olefinic feed and the metal carbene catalyst are contacted in a hydrocarbon solvent inert to undergoing olefin metathesis.

16. The process of claim 9, wherein the linear olefin dimer has a structure represented by

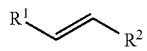

wherein $R^1$ and $R^2$ are independently selected alkyl groups having from 10 to 24 carbon atoms.

17. The process of claim 1, wherein the wax composition is a partially hydrogenated reaction product.

18. The process of claim 17, further comprising contacting the linear olefin dimer with a hydrogenation catalyst under hydrogenation reaction conditions, and hydrogenating at least a portion of the linear olefin dimer to form a linear paraffin product.

* * * * *